(12) United States Patent  
Dilmaghanian et al.

(10) Patent No.: US 8,167,660 B2  
(45) Date of Patent: May 1, 2012

(54) CONNECTOR ASSEMBLIES FOR USE WITH IMPLANTABLE MEDICAL DEVICES

(75) Inventors: Farshid Dilmaghanian, Foothill Ranch, CA (US); Hugh Cook, Foothill Ranch, CA (US); Daniel D. Poon, Foothill Ranch, CA (US); Shahriar Sean Madanipour, Foothill Ranch, CA (US); Rob Sjostedt, Foothill Ranch, CA (US); Bill Nissim, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 0 days.

(21) Appl. No.: 12/876,775

(22) Filed: Sep. 7, 2010

(65) Prior Publication Data

US 2011/0059639 A1 Mar. 10, 2011

Related U.S. Application Data

(60) Provisional application No. 61/240,157, filed on Sep. 4, 2009.

(51) Int. Cl.  
  *H01R 24/04* (2006.01)
(52) U.S. Cl. ........................................................ 439/669
(58) Field of Classification Search .................. 439/659, 439/669  
See application file for complete search history.

(56) References Cited

U.S. PATENT DOCUMENTS

| 4,934,366 | A | 6/1990 | Truex et al. |
| 6,430,442 | B1 | 8/2002 | Peters et al. |
| 6,895,276 | B2 | 5/2005 | Kast et al. |
| 7,601,033 | B2 * | 10/2009 | Ries et al. ................. 439/669 |
| 2008/0246231 | A1 | 10/2008 | Sjostedt et al. |

OTHER PUBLICATIONS

International Search Report completed and mailed May 30, 2011 from corresponding International Application No. PCT/US2010/048000 filed Sep. 7, 2010 (3 pages).

Written Opinion completed and mailed May 30, 2011 from corresponding International Application No. PCT/US2010/048000 filed Sep. 7, 2010 (4 pages).

* cited by examiner

*Primary Examiner* — Phuong Dinh  
(74) *Attorney, Agent, or Firm* — Klein, O'Neill & Singh, LLP

(57) ABSTRACT

Connector assemblies for use to concurrently transmit multiple signals or sources. The connector assemblies are generally formed by coupling a plurality of ring contacts, sealing rings, and spring contact elements together with at least one holding ring to form a connector having a common bore for receiving a lead cable. Contact grooves or spring chambers for positioning the spring contact elements are formed in part by assembling multiple components together. The connector assemblies may be used in a number of industries and applications.

20 Claims, 16 Drawing Sheets

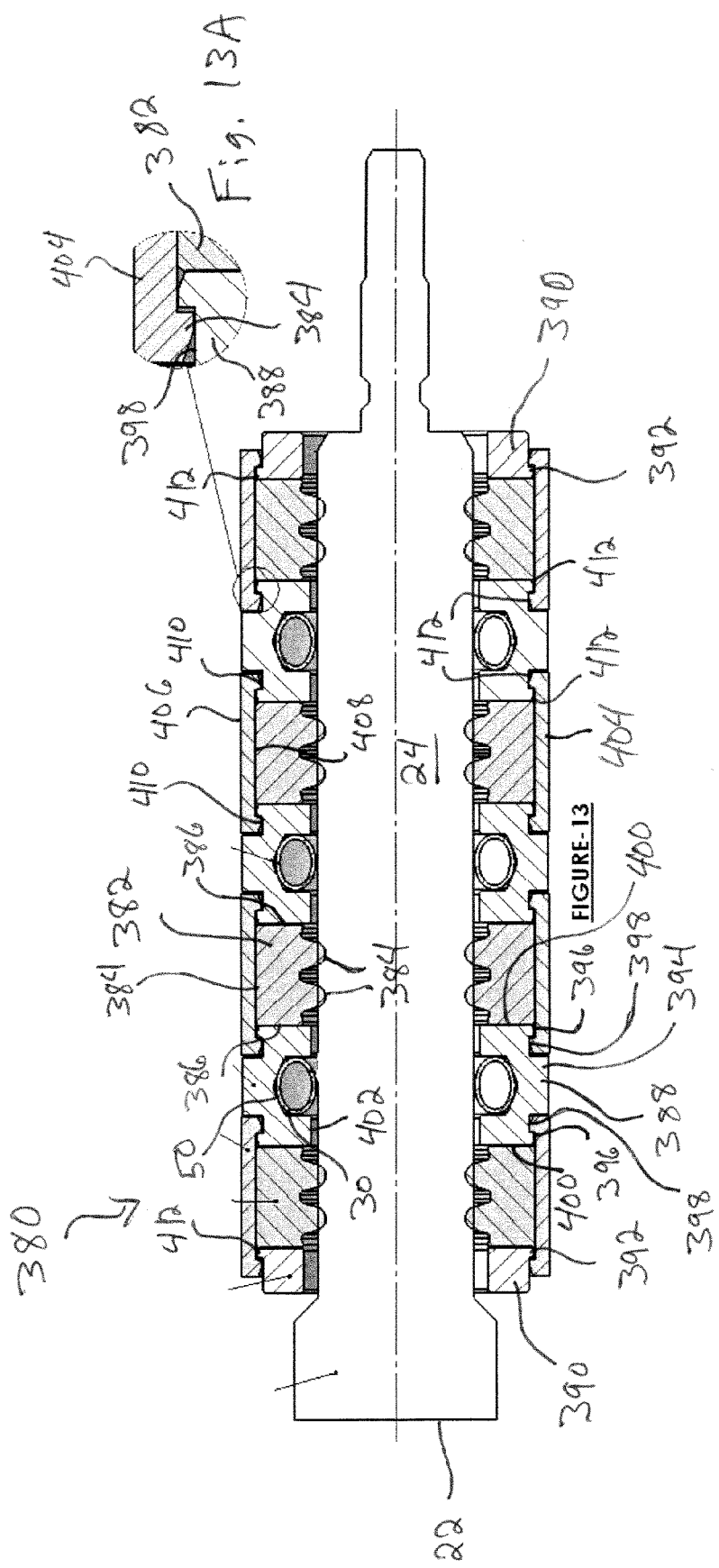

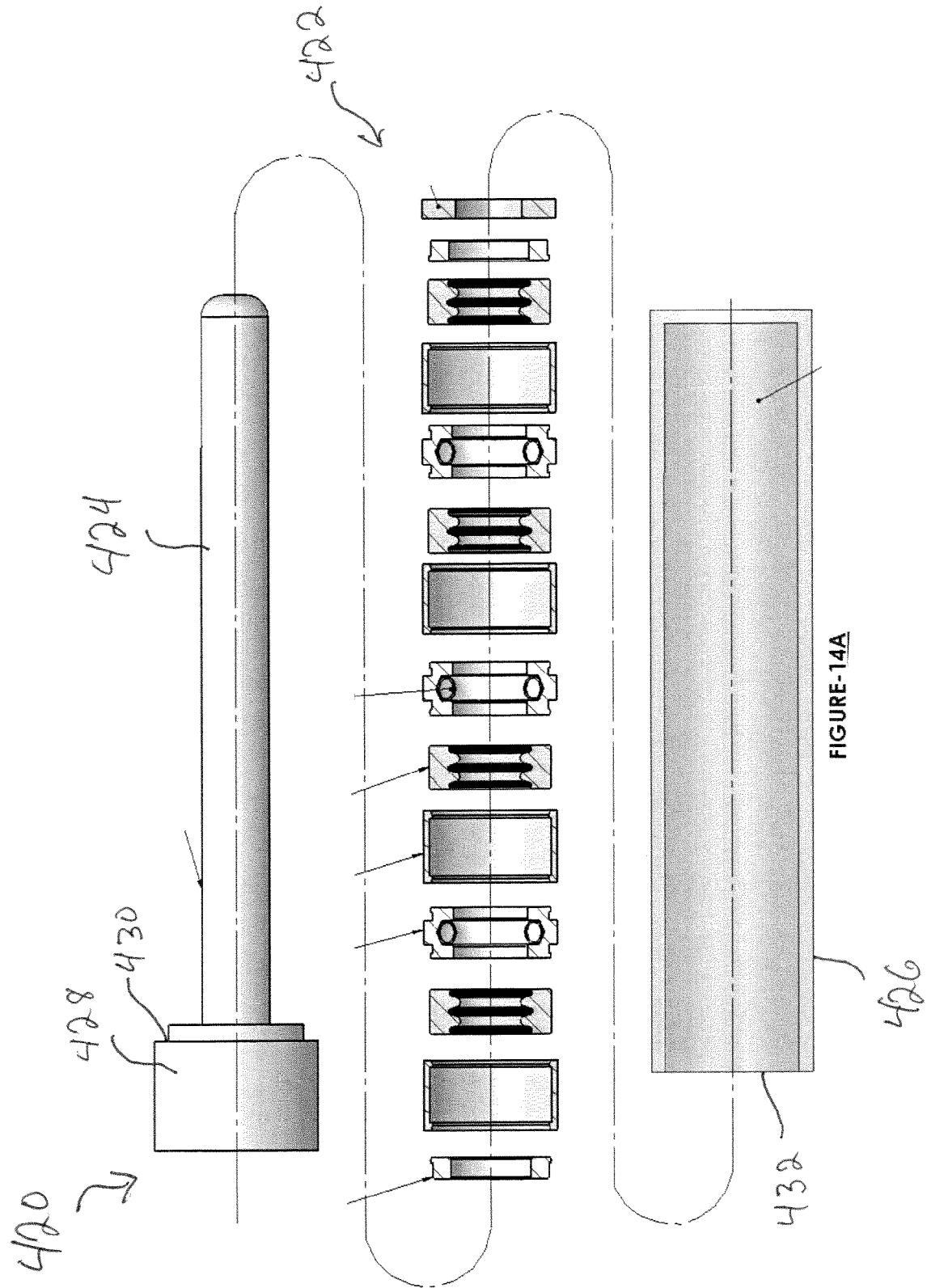

CONNECTOR ASSEMBLIES FOR USE WITH IMPLANTABLE MEDICAL DEVICES

CROSS-REFERENCE TO RELATED APPLICATION

This application claims priority to provisional application Ser. No. 61/240,157, filed on Sep. 4, 2009, the entire contents of which are hereby expressly incorporated by reference.

TECHNICAL FIELD

The present assembly, device, and method relate to in-line connector assemblies having one or more spaced conductive elements, particularly connector assemblies for use with implantable medical devices with applications in other industries, such as electronics, aviation, and automotive

BACKGROUND

Implantable medical devices are commonly used to provide electrical stimulation to body tissues, monitor physiologic conditions, and provide alternative treatments to drugs. Examples of implantable medical devices include implantable cardio defibrillators, pacemakers, and programmable neuro-stimulator pulse generators, which are collectively referred to herein as implantable medical devices or IMDs. IMDs typically incorporate a hermetically sealed housing enclosing a power source and electronic circuitry. The sealed housing is also known as a "can."

A header assembly is connected to the can. The header assembly includes a generally cylindrical receptacle for a medical lead cable. The receptacle includes spaced electrical contact elements that are electrically coupled to the electronic circuits or to the power source located inside the can via conductive terminals or leads. The header assembly provides a means for electrically communicating, via the external medical lead cable, between the electronic circuits or power source located inside the device and the area on the anatomy where the stimulation is applied.

In one preferred embodiment, the electrical contact elements are canted coil springs within circular conductive housings. The electrical contact elements have elastomeric seals in between them to prevent the intrusion of body fluids from affecting the electrical performance of the IMD.

Industry-wide standards have been adopted for, among other things, the dimensions, contact spacing, etc. for the medical lead cable and the receptacle. Furthermore, it is desirable to maintain good electrical contact between the header assembly and the medical lead cable during the life of the implantable medical device. It is not desirable for the medical lead cable to disconnect from the receptacle, because it would then be impossible to provide electrical stimulation to the stimulation site. However, it is desirable for the medical lead cable to be removable from the receptacle while implanting and/or programming the IMD, and for replacing the IMD when necessary.

The following U.S. patent applications provide further information regarding connector assemblies for use with implantable medical devices: Ser. No. 12/100,646, filed on Apr. 10, 2008; Ser. No. 12/102,626, filed on Apr. 14, 2008; Ser. No. 12/062,895; filed on Apr. 4, 2008; and 61/171,043, filed on Apr. 20, 2009.

SUMMARY

The various embodiments of the present connector assemblies for use with implantable medical devices have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present connector assemblies for use with implantable medical devices includes the realization that it is desirable to increase the number of electrical contact elements within a header assembly of an IMD. Each electrical contact element provides a path for electric current to be delivered from within the IMD, through a lead, to a stimulation site. When more contact elements are provided, more leads can be provided, and electrical stimulation can be delivered to more locations. However, IMDs are desirably as small as possible, because they are designed to be implanted under the skin. Thus, it is not desirable to simply increase the size of IMDs in order to accommodate more contact elements. One possible solution, then, is to decrease the spacing between contact elements. But doing so shortens the electrical path between contact elements, which can cause arcing. Also, moving the contact elements closer to one another shortens the width of the elastomeric insulating spacers between contact elements, which can lead to fluid leaking into the IMD. The present embodiments address these problems.

Another aspect of the present connector assemblies for use with implantable medical devices includes the realization that during the manufacturing integration process, the contact elements and seals must be kept aligned coaxially and with the proper compression on the seals and with the proper contact spacing. Thus, the manufacturing integration process is typically complex, difficult, costly, time-consuming and not always repeatable, especially as the number of contact elements and seals for devices increases. Accordingly, there is a need for a receptacle that not only meets the challenges associated with implantable applications, but is also easier to manufacture than a variety of existing receptacles. There is also a need for a receptacle that is easily adaptable with existing IMDs.

One embodiment of the present connector assemblies comprises a plurality of electrically conductive ring contact elements arranged coaxially. Each ring contact element includes an annular groove about its inner circumference. The connector assembly further comprises a plurality of electrically conductive garter-type spring contact elements positioned within the grooves. The connector assembly further comprises a plurality of electrically non-conductive seal rings interposed between adjacent ones of the ring contact elements and arranged coaxially therewith. The ring contact elements and the seal rings engage one another in an interlocking fashion to resist separation of the ring contact elements and the seal rings from one another in the absence of applied compression.

Another embodiment of the present connector assemblies comprises a plurality of electrically conductive ring contact elements arranged coaxially. Each ring contact element includes an annular groove about its inner circumference. The connector assembly further comprises a plurality of electrically conductive garter-type spring contact elements positioned within the grooves. The connector assembly further comprises a plurality of electrically non-conductive seal rings interposed between adjacent ones of the ring contact elements and arranged coaxially therewith. Each of the seal rings protrudes radially beyond outer surfaces of the ring contact elements.

Another embodiment of the present connector assemblies comprises a method of assembling a connector assembly. The method comprises positioning a plurality of electrically conductive garter-type spring contact elements within grooves of a plurality of electrically conductive ring contact elements. The method further comprises interlocking a first seal ring with a first one of the ring contact elements such that the first seal ring and the first ring contact element are coaxial, the first seal ring being electrically non-conductive. The method further comprises interlocking successive seal rings and ring contact elements in coaxial alignment, and with the seal rings interposed between adjacent ones of the ring contact elements, until a desired number of ring contact elements have been added. The interlocked seal rings and ring contact elements resist separation of the ring contact elements and the seal rings from one another in the absence of applied compression.

BRIEF DESCRIPTION OF THE DRAWINGS

The various embodiments of the present connector assemblies will be discussed in detail with an emphasis on highlighting the advantageous features. These embodiments depict the novel and non-obvious connector assemblies shown in the accompanying drawings, which are for illustrative purposes only. These drawings include the following figures, in which like numerals indicate like parts:

FIG. 1A is a detail view of the circled portion of FIG. 1;

FIG. 2A is a detail view of the circled portion of FIG. 2;

FIG. 3A is a detail view of the circled portion of FIG. 3;

FIG. 4A is a detail view of the circled portion of FIG. 4;

FIG. 5A is a detail view of the circled portion of FIG. 5;

FIG. 6A is a detail view of the circled portion of FIG. 6;

FIG. 7A is a detail view of the circled portion of FIG. 7;

FIG. 8A is a detail view of the circled portion of FIG. 8;

FIG. 9A is a detail view of the circled portion of FIG. 9;

FIG. 10A is a detail view of the circled portion of FIG. 10;

FIG. 11A is a detail view of the circled portion of FIG. 11:

FIG. 12A is a detail view of the circled portion of FIG. 12;

FIG. 13 is a front cross-sectional view of another embodiment of the present connector assembly for use with IMDs or alternatively for transmitting multiple signals in an electrical-related application;

FIG. 13A is a detail view of the circled portion of FIG. 13;

FIG. 14A is a front cross-sectional exploded view of one embodiment of a kit including a connector assembly for use with IMDs or alternatively for transmitting multiple signals in an electrical-related application;

DETAILED DESCRIPTION

Figure 1:
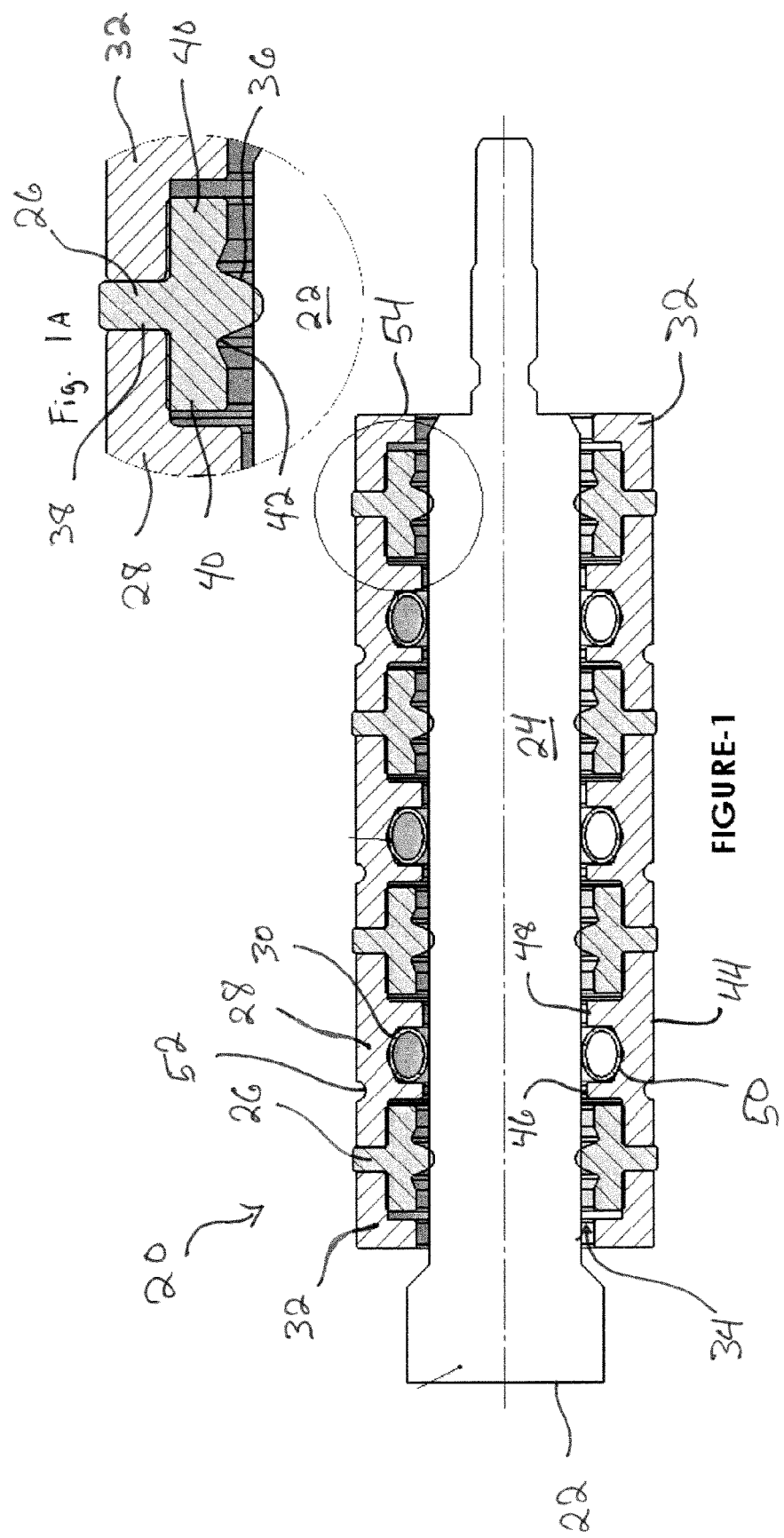
FIG. 1 is a front cross-sectional view of one embodiment of the present connector assembly for use with implantable medical devices (IMDs) or alternatively for transmitting multiple signals in an electrical-related application.

The following detailed description describes the present embodiments with reference to the drawings. In the drawings, reference numbers label elements of the present embodiments. These reference numbers are reproduced below in connection with the discussion of the corresponding drawing features.

The embodiments of the present connector assemblies for use with implantable medical devices are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece. Depending on the context of how it is used, the word "integral" or "integrally" can also include separately formed components that function together as a single unit.

The following discussion focuses on connector assemblies for use with implantable medical devices. However, the connector assemblies discussed herein are useful in a wide variety of applications, including medical, automotive, electrical transmission, aerospace, consumer electronics, consumer products, etc. For example, the present connector assemblies may be used as battery terminals, for transmitting electronic data, or as a socket for transmitting audio signals, etc. Accordingly, the present embodiments encompass generally connectors for allowing transmissions between a source generator and a source receiver, or for acting as a conduit between two sources, regardless of the particular application.

FIG. 1 illustrates one embodiment of the present connector assemblies for use in transmitting electrical signals, such as for implantable medical devices (IMDs). The assembly 20 is configured to receive a medical lead cable 22, which includes a plurality of electrical terminals (not shown) interposed between lead insulators (not shown). The lead cable 22 further comprises a lead body 24 for carrying a plurality of electrode leads (not shown). An opposite end of each lead includes electrode terminals for providing electrical stimulation to body tissues at a stimulation site. The number of electrode leads and corresponding number of electrical terminals may vary depending upon the particular implant application. The number of electrode leads also corresponds to the number of electrical ring contacts in the connector assembly 20, as further discussed below. Applications of the present connector assemblies include unipolar, bipolar, and multipolar applications by simply changing the number of components used to make the connector assembly 20.

The connector assembly 20 comprises a plurality of electrically non-conductive seal rings 26, electrically conductive ring contact elements 28 (also referred to as contact rings 28), and electrically conductive garter-type spring contact elements 30 (also referred to as spring contacts 30) arranged coaxially. Holding rings 32, which may be electrically conductive or electrically non-conductive, cap opposite ends of the assembly 20. The assembly 20 forms a cylindrical passage 34 or common bore for receiving the lead cable 22. The assembly 20 may also be viewed as comprising a series of alternating seal rings 26 and ring contact elements 28 to transmitting corresponding number of electrical signals or sources.

Each ring contact element 28 and each spring contact element 30 is configured to conduct an electric current or signal, which for convenience will be referred to herein as current. However, other signals such as audio signals, electrical pulses, and voltages may be substituted. The current originates inside an IMD housing (not shown) or a source supply, then flows through a conductor (not shown) located within the housing to a corresponding ring contact element 28. The current then flows to a corresponding spring contact element 30, which is in mechanical and electrical contact with a corresponding terminal (not shown) on the electrical lead 22 body 24. The current then flows to a corresponding electrode lead located inside the lead body 24, and then to a corresponding electrode terminal on the opposite end of the lead cable 22, which applies the desired electrical stimulation to body tissues at the stimulation site. The seal ring elements 26 are electrically insulative, and resist the flow of current between adjacent contact rings 28. Exemplary conductors incorporated in an IMD are further discussed in application Ser. No. 12/100,646, filed on Apr. 10, 2008; Ser. No. 12/102,626, filed on Apr. 14, 2008; Ser. No. 12/062,895: filed on Apr. 4, 2008; and 61/171,043, filed on Apr. 20, 2009, the contents of each of which are expressly incorporated herein by reference.

With reference to FIG. 1A, the cross-section of each seal ring 26 is shaped substantially as a cross or plus sign. Each seal ring 26 includes an inwardly extending, annular flange 36 that is configured to abut the lead cable 22 in an interference fit to provide a liquid-tight seal at the interface. Each seal ring 26 further includes an outwardly extending annular flange 38 that is configured to seat between and abut adjacent contact rings 28 in a liquid-tight seal at each interface. Oppositely extending arms 40 of each seal ring 26 abut inner surfaces of adjacent contact rings 28 in an interference fit to provide a liquid-tight seal at each interface. Sealing thus advantageously occurs at multiple interfaces between the seal rings 26 and the contact rings 28. The seals resist intrusion of bodily fluids into the connector assembly 20 and into the can.

With further reference to FIG. 1A, a height of each outwardly extending annular flange 38 is greater than a wall thickness of the contact rings 28. An outer end of each flange 38 thus protrudes from the assembly 20. The protruding flanges 38 are configured to bear against an inner surface of a header assembly (not shown) in a liquid tight seal at the interface. The seals by the protruding flanges 38 against inner surface of the header assembly provide further resistance to intrusion of bodily fluids.

With continued reference to FIG. 1A, the cross-section of each seal ring 26 further includes undercuts 42 at the junction of each arm 40 with the inwardly extending annular flange 36. The undercuts 42 create additional space to accommodate side-to-side deformation of the inwardly extending annular flange 36 as the electrical lead 22 is inserted and withdrawn from the assembly 20. The interference fit between the electrical lead 22 and the seal rings 26 urges the inwardly extending annular flanges 36 to flex side-to-side as the electrical lead 22 is inserted and withdrawn from the assembly 20. The undercuts 42 provide empty space into which the flanges 36 can deform, which lessens the insertion and removal force for the electrical lead 22. The lessened insertion force reduces the likelihood that components might be damaged during assembly, and the lessened removal force facilitates disassembly in the event the IN/ID requires repair or replacement.

With reference again to FIG. 1. each contact ring 28 includes an outer cylindrical portion 44 and first and second spaced annular flanges 46. 48 that extend inwardly toward a central axis. Inner diameters of the inwardly extending flanges 46. 48 are large enough so that the contact rings 28 remain spaced from the electrical lead body 24. The flanges 46. 48 together with a base 49 form a double-walled groove 50. In the illustrated embodiment, the base 49 of the groove 50 is V-shaped. but in other embodiments the groove 50 could have any shape. such as flat or sloped relative to the flanges. The groove 50 receives the spring contact element 30, which can be a garter-type radial or axial canted-coil spring. The spring 30 may be. for example. of the type commercially available from Bal Seal Engineering of Foothill Ranch. California. The spring 30 is sized so that it is positioned by the groove 50 along its two axial ends and establishes contact about its inner circumference with the electrical lead 22 and about its outer circumference with the contact ring 28. The double-walled groove 50 nestles the spring contact 30 so that it stays axially aligned as the electrical lead 22 is inserted during the assembly process.

In the illustrated embodiment, each of the first flanges 46 has a first narrower width and each of the second flanges 48 has a second wider width relative to the first width. However. in alternative embodiments the relative widths of the flanges 46, 48 could be reversed, or the flanges 46. 48 could have equal widths. Also, in the illustrated embodiment the width and position of each first flange 46 corresponds to a width and position of an outer annular groove 52 about the outer surface of each contact ring 28. The groove 52 thus provides an external indicator of the location of each first flange 46. This feature is discussed in more detail below.

In certain embodiments, the spring contacts 30 are similarly sized so that when the electrical lead 22 is inserted into the assembly 20 each spring 30 is deflected by the electrical lead 22 to about 5% and up to about 50% of its total radial deflection with up to about 40% being preferred. This deflection range ensures that a sufficient spring contact force is generated between the spring contacts 30 and the contact rings 28, and between the spring contacts 30 and the terminals on the electrical lead 22, for transferring electric current between the contact rings 28 and the terminals, or between a first source and a second source.

With reference to FIG. 1, each holding ring 32 is substantially cylindrical with an inwardly extending flange 54 at its outer edge. The flanges 54 are sized so that the holding rings 32 are spaced from the electrical lead 22.

The outer surface of each contact ring 28 includes the annular groove 52. The contact rings 28 are preferably fabricated so that the groove 52 is located in the same place along the length of each contact ring 28. As mentioned above, the location of each groove 52 may also correspond to the location of each first flange 46. The grooves 52 provide visual indicators on the outside of the assembly 20 that assist in properly locating the spring contacts 30 within the assembly 20, as discussed below.

During the assembly process, compression is applied to the ends of the assembly 20. The applied force moves the contact rings 28 closer to one another, which compresses the width of the outwardly extending flange 38 of each sealing ring 26, and also moves the spring contacts 30 closer to one another. Because of axial play during assembly of the alternating stack of components, the grooves 52 provide an external marker on the assembly 20 to facilitate alignment, measurements, and spacing. During the assembly process, the distance between adjacent grooves 52 can be measured to ensure that the spring contacts 30 within the assembly 20 are properly located and/or whether any of the outwardly extending flanges are overly compressed. Thus, the distance between adjacent grooves 52 can be determined according to the design of the assembly 20, then checked during assembly to ensure appropriate spacing.

In one embodiment of a method of assembling the connector assembly 20, the spring contacts 30 are first placed within the grooves 50 in the contact rings 28. A first holding ring 32 is then engaged with a first seal ring 26 in coaxial alignment, followed by a first contact ring 28 engaging the first seal ring 26 in coaxial alignment. Successive seal rings 26 and contact rings 28 are then added in coaxial alignment until a desired number of contact rings 28 and seal rings 26 have been added. A second holding ring 32 is then engaged in coaxial alignment with the last added seal ring 26, opposite the first holding ring 32. In certain embodiments, the assembly process may be performed by hand without tools. Alternatively, a dowel or assembly pin (not shown) may be used. The dowel or pin first receives a holding ring 32, and then the other components are slid onto the pin and into engagement with the earlier placed components.

The assembled connector assembly 20 may then be placed into a mold cavity and over-molded with an implantable-grade polymer or elastomer, such as epoxy or silicone. The connector assembly 20 can also be inserted into a pre-molded header, which resembles a housing having a cavity for receiving the connector assembly 20 and one or more openings for placing the connector assembly 20 into the pre-molded header. The one or more openings are then backfilled or sealed, typically after attaching or welding the conductors from the sealed housing to the contact rings 28, to complete the assembly. When use with other devices, such as a music or audio player, the connector assembly 20 may be placed into a housing and fixed in place my mechanical means, such as straps, fasteners, etc. For example, the connector assembly 20 may be equipped with two ring contact elements 28 and two spring contact elements 30 for a stereo output application.

The contact rings 28 are made from an electrically conductive material, which may for example be a steel material, such as stainless steel. Alternatively, the contact rings 28 may be made from titanium, noble metals such as platinum, or conventional implantable grade materials with noble metal coatings, such as platinum over stainless steel. The holding rings may be made from the same material as the contact rings 28. Alternatively, the holding rings may be made from an implantable-grade, electrically non-conductive, rigid plastic material, such as PolyEtherEtherKetone (PEEK). The seal rings 26 are preferably made from an electrically non-conductive medical grade polymer or elastomer, such as silicone. The seal rings 26 are thus flexible and resilient, and enable a range of interference fits, which provides manufacturing flexibility in terms of tolerance and accuracy.

Thus, examples of the present assembly, device, and method include an in-line connector assembly comprising at least two alternating seal assemblies and ring contact elements having a common bore; wherein each of the at least two ring contact elements comprises an internal spring groove and wherein an external groove formed on each of the at least two ring contact elements are configured to locate relative positions of the two internal spring grooves. In another example, a connector assembly is provided wherein external markers, such as external grooves 52, are configured to located relative positions of internal spring grooves 50, which are not visible to a user or technician. Thus, another embodiment of present device, assembly, and method is a combination lead cable inserted into a common bore of an in-line connector, and wherein external grooves on the in-line connector indicate relative positions of internal spring grooves and electrical terminals. The latter being part of the lead cable.

FIGS. 2-14 illustrate alternative embodiments of the present connector assemblies, devices, and methods. These alternative embodiments share many similarities with the embodiment described above and shown in FIG. 1, and provide many of the same functionalities and advantages. Accordingly, to avoid repetition, the following discussion focuses on the features and advantages of FIGS. 2-14 that differ from the embodiment of FIG. 1. Further, many of the embodiments of FIGS. 2-14 share many similarities and advantages with one another. Thus, again to avoid repetition, some features and advantages achieved by a particular embodiment may not be discussed with respect to that embodiment where the same features and advantages have already been described with respect to a previous embodiment. Furthermore, where specific features are discussed with respect to one embodiment but not another, the same specific features may be understood to be usable and interchangeable with the non-discussed embodiment provided the specific features do not functionally conflict or are incompatible.

Figure 2:
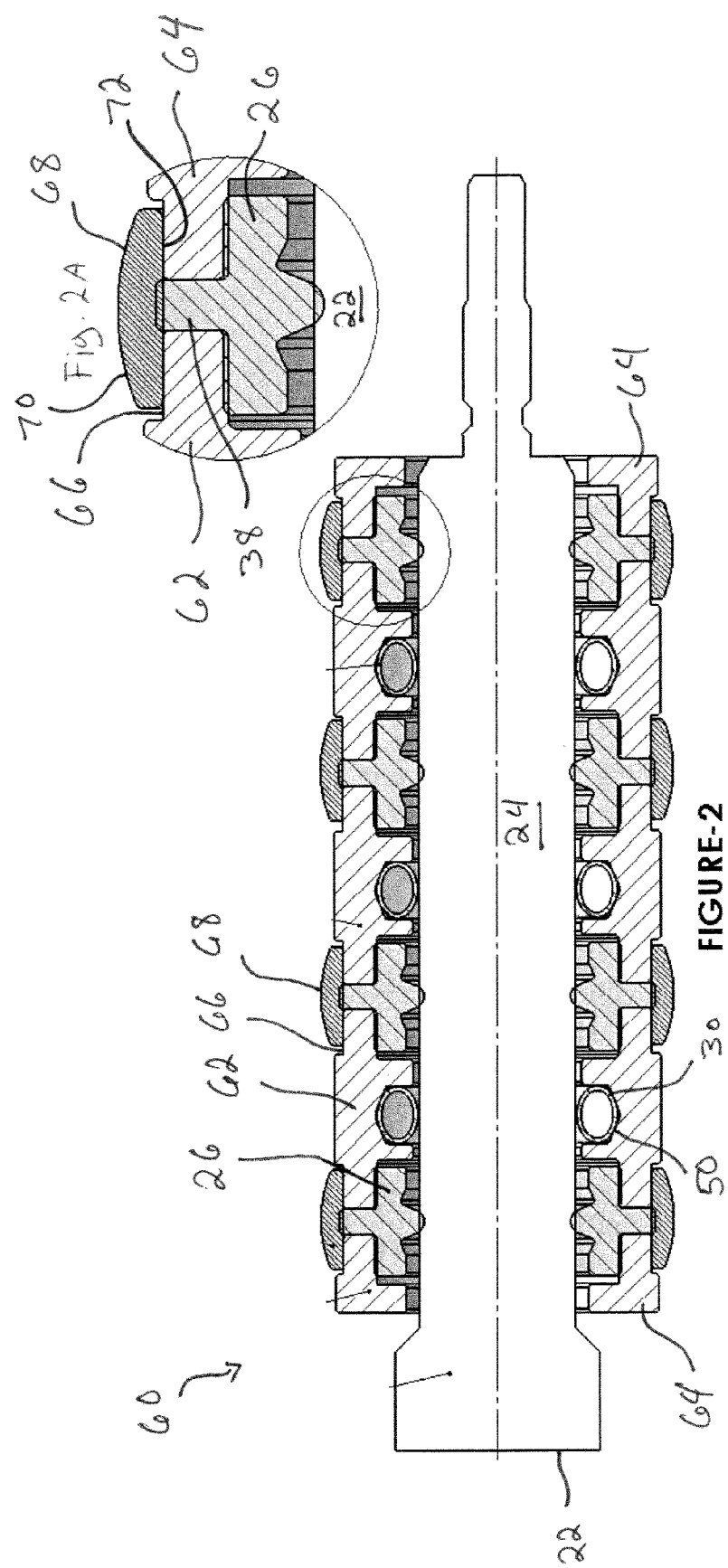
FIG. 2 is a front cross-sectional view of another embodiment of the present connector assembly for use with IMDs or alternatively for transmitting multiple signals in an electrical-related application.

With reference to FIG. 2, the connector assembly 60 includes contact rings 62 having a cross-sectional shape that is similar to that of FIG. 1. However, in the embodiment of FIG. 2 each contact ring 62 includes a decreased wall thickness at either end. Each holding ring 64 also includes a decreased wall thickness at its end. When the assembly 60 is assembled, adjacent contact rings 62 form an external groove 66 at the junction of the decreased wall thickness portions. Adjacent holding rings 64 and contact rings 62 also form a groove 66 (FIG. 2A) at the junction of the decreased wall thickness portions.

The grooves 66 receive annular bands 68 of an electrically insulative material, such as rubber, silicone, a thermoplastic material (TPE), or an implantable-grade, electrically non-conductive, rigid plastic material, such as PolyEtherEtherKetone (PEEK). With reference to FIG. 2A, the insulative bands 68 include a convex outer surface 70, giving the cross-section of each band 68 a variable thickness, with a maximum thickness occurring at the center of the band's width and tapering down to minimum thicknesses at either end of the band 68. In other embodiments, the outer surface features differ. For example, the outer surface features can include two humps, random protrusions, or arrays of arcuate surfaces. An inner surface 72 of each band 68, which abuts the contact rings 62, is generally flat. A width of each band 68 may substantially correspond to the width of its groove 66, or may be slightly narrower than its groove 66.

The insulative bands 68 provide numerous advantages. For example, the bands 68 reduce the chance that an electrical arc will occur between adjacent contact rings 62. Adjacent contact rings 62 can thus be placed closer together, increasing the pitch of the assembly 60 and enabling more contact rings 62 to be included in the assembly 60. The bands 68 also provide additional sealing between adjacent contact rings 62, supplementing the sealing provided by the sealing rings 26. The bands 68 further provide a stabilizing compressive force that assists in maintaining coaxial alignment of the components. The bands 68 also provide sealing engagement with the inner surfaces of a pre-molded header or housing which the connector assembly 60 is seated. These advantages are discussed further below.

The insulative bands 68 abut the outer surfaces of the adjacent contact rings 62, thereby providing sealing at the interfaces. The insulative bands 68 may be sized for an interference fit with the contact rings 62 to increase both their sealing effect and their ability to maintain coaxial alignment of the components.

The insulative bands 68 are also configured to provide sealing engagement with a pre-molded header (not shown) or housing in which the connector assembly seats. The size, position and cross-sectional shape of the bands 68 facilitates sealing. The bands 68 protrude outwardly beyond the maximum outside diameter of the contact rings 62. Further, the bands 68 include a convex outer surface 70, as described above. And, a width of each band 68 is slightly less than a width of its respective groove 66 (FIG. 2A). Thus, when the connector assembly 60 is inserted within the pre-molded header, the bands 68 are configured to compress and deform as and bear against the inner surfaces of the header. Deformation may occur as the convex outer surfaces flatten and material is displaced into the empty spaces of the grooves 66.

The abutment of the insulative bands 68 against the contact rings 62 also blocks the potential pathway for an electrical arc between adjacent ends of the contact rings 62. The insulative bands 68 effectively lengthen the shortest possible electrical arc pathway. With reference to FIG. 2A, in the absence of the insulative bands 68, the shortest possible electrical arc pathway is the distance between adjacent contact ring ends, which is approximately the width of the outwardly extending annular flange 38 on the sealing ring 26. With the insulative bands 68 positioned in the grooves 66, the shortest possible electrical arc pathway is the distance between adjacent exposed portions of the contact rings 62, which is approximately the width of the band 68. The width of the band 68 is considerably greater than the width of the flange 38 on the seal ring. Since the potential for an electrical arc to occur decreases as the path length increases, the insulative bands 68 reduce the chance that an electrical arc will occur between adjacent contact rings 62. Adjacent contact rings 62 can thus be placed closer together, increasing the pitch of the assembly 60 and enabling more contact rings 62 to be included in the assembly 60. Thus, a feature of the present connector assembly is an insulative band 68 having a width for increasing an electrically conductive distance between two adjacent ring contact elements. As shown, the distance that has been increased is understood to be the distance of the width of the band 68 less the width of the outwardly extending flange 38 of the seal ring that is being compressed between adjacent ring contact elements.

In one method of assembling the connector assembly 60 of FIG. 2, the spring contacts 30 are first placed within the grooves 50 in the contact rings 62. A first holding ring 64 is then engaged with a first seal ring 26 in coaxial alignment, followed by a first insulative band 68 engaging the first holding ring 64 and the first seal ring 26 in coaxial alignment, with the first insulative band 68 extending around the outside of the first holding ring 64 and the first seal ring 26. A first contact ring 62 is then engaged with the first seal ring 26 and the first insulative band 68 in coaxial alignment such that the first insulative band 68 is positioned within the groove 66 formed between the first holding ring 64 and the first contact ring 62. Successive seal rings 26, insulative bands 68 and contact rings 62 are then added in coaxial alignment until a desired number of contact rings 62 have been added. A second holding ring 64 is then engaged in coaxial alignment with the last added seal ring and insulative band 68, opposite the first holding ring 64. In certain embodiments, the assembly 60 process may be performed by hand without tools. Alternatively, a dowel or assembly pin (not shown) may be used. The dowel or pin first receives a holding ring 64, and then the other components are slid onto the pin and into engagement with the earlier placed components.

In alternative methods of assembling the connector assembly 60 of FIG. 2, the order of operations or assembly may differ from that described above. For example, instead of engaging the first holding ring 64 with the first seal ring 26, followed by the first insulative band 68 engaging the first holding ring 64 and the first seal ring 26, an alternative method may engage the first holding ring 64 with the first insulative band 68, followed by the first seal ring 26 engaging the first holding ring 64 and the first insulative band 68. The first contact ring 62 is then engaged with the first seal ring 26 and the first insulative band 68, and successive insulative bands 68, seal rings 26 and contact rings 62 are then added until the desired number of contact rings 62 have been added. A second holding ring 64 is then engaged in coaxial alignment with the last added seal ring 26 and insulative band 68, opposite the first holding ring 64.

In still further alternative methods of assembling the connector assembly 60 of FIG. 2, the insulative bands 68 may be added only after the remaining components have been assembled. Thus, the first holding ring 64 may be engaged with the first seal ring 26, followed by the first contact ring 62 engaging the first seal ring 26. Successive seal rings 26 and contact rings 62 are then added until the desired number of contact rings 62 have been added. A second holding ring 64 is then engaged in coaxial alignment with the last added seal ring 26, opposite the first holding ring 64. The insulative bands 68 are then added by expanding each one sufficiently that it can pass over the assembly 60 and be seated within its respective groove 66. This method requires that the insulative bands 68 be constructed of a flexible and resilient material.

Figure 3:
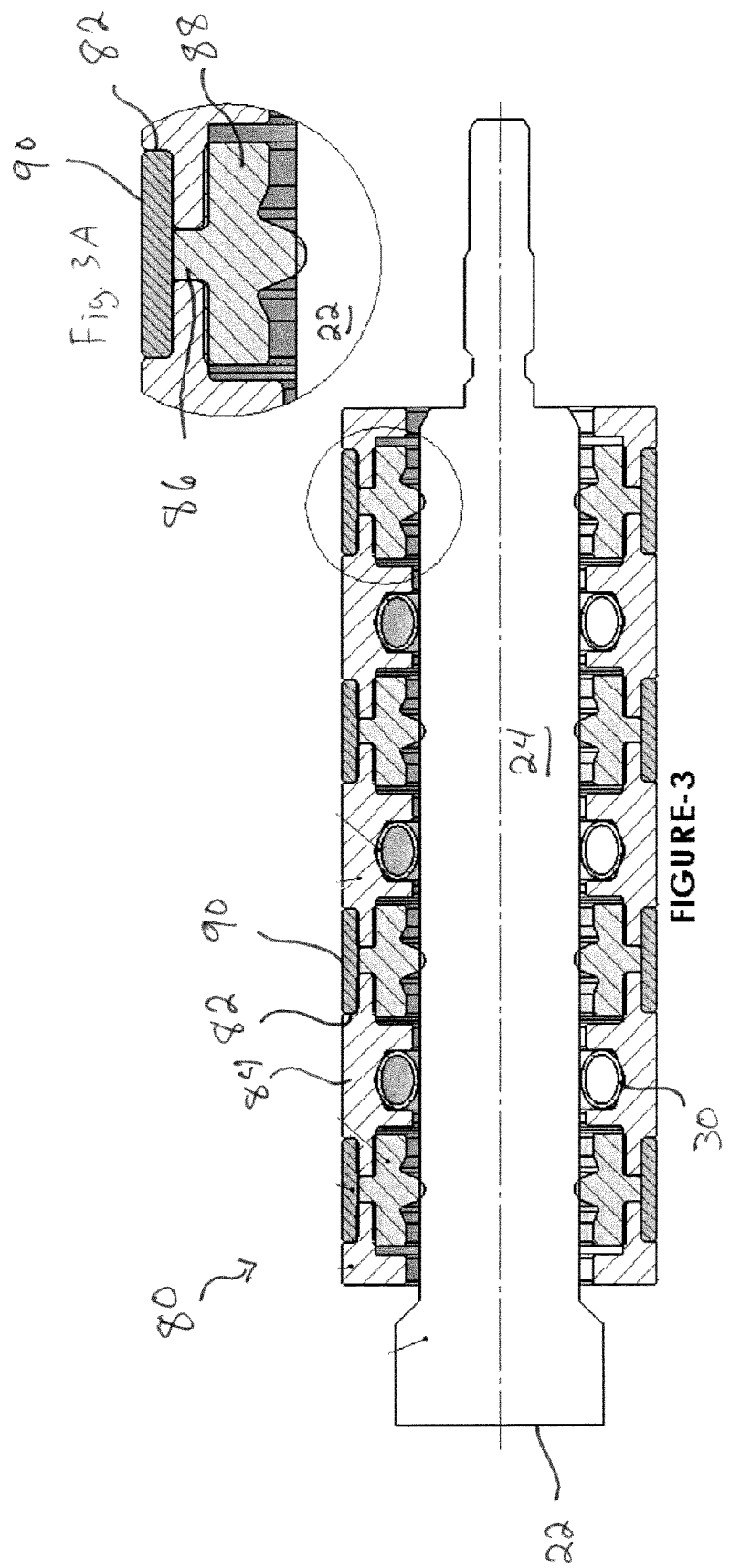
FIG. 3 is a front cross-sectional view of another embodiment of the present connector assembly for use with IMDs or alternatively for transmitting multiple signals in an electrical-related application.

FIG. 3 illustrates another alternative embodiment 80 of the present connector assemblies. The embodiment 80 of FIG. 3 is similar to that of FIG. 2, but in contrast to the embodiment 60 of FIG. 2, the grooves 82 are deeper. The wall thickness of the contact rings 84 at their ends is thus less than the wall thickness of the contact rings 62 of FIG. 2 at their ends, and the outwardly extending annular flange 86 on the sealing ring 88 has a correspondingly shorter height (FIG. 3A).

The grooves 82 receive annular bands 90 of an electrically insulative material, which may be any of the materials discussed above with respect to the insulative bands 68 of FIG. 2. However, in contrast to the embodiment 60 of FIG. 2, the insulative bands 90 have a constant thickness that corresponds to the depth of the groove 82. The insulative bands 90 also have a width that corresponds to the width of the groove 82 in the fully assembled configuration. The insulative bands 90 thus substantially fill their respective grooves 82.

The insulative bands 90 of FIG. 3 provide the same advantages of the insulative bands 90 of FIG. 2. However, because the insulative bands 90 are sized to substantially fill their respective grooves 82 in the fully assembled configuration, they also assist in controlling compressive displacement of the contact rings 84 during assembly and during lead insertion. As mentioned above, during the assembly process some compression is applied to the assembly 80. The compression displaces the contact rings 84 so that they get closer together as the width of each outwardly extending annular flange 86 narrows. As the contact rings 84 move closer together, the width of each groove 82 narrows. If the insulative bands 90 are constructed of a material that is substantially non-compressible, the bands 90 will resist further displacement of the contact rings 84 once sufficient compressive force is applied to narrow the grooves 82 until their width matches that of the bands 90. Thus, the bands 90 and the grooves 82 can be manufactured to tight tolerances to provide a reliable means for ensuring that the proper compression is achieved within the assembly so that the contact springs 30 are properly located. As shown, the bands 90 are also understood to thwart, prevent, or otherwise make arcing between adjacent contact ring elements more difficult than a comparable device without the annular bands.

Figure 4:
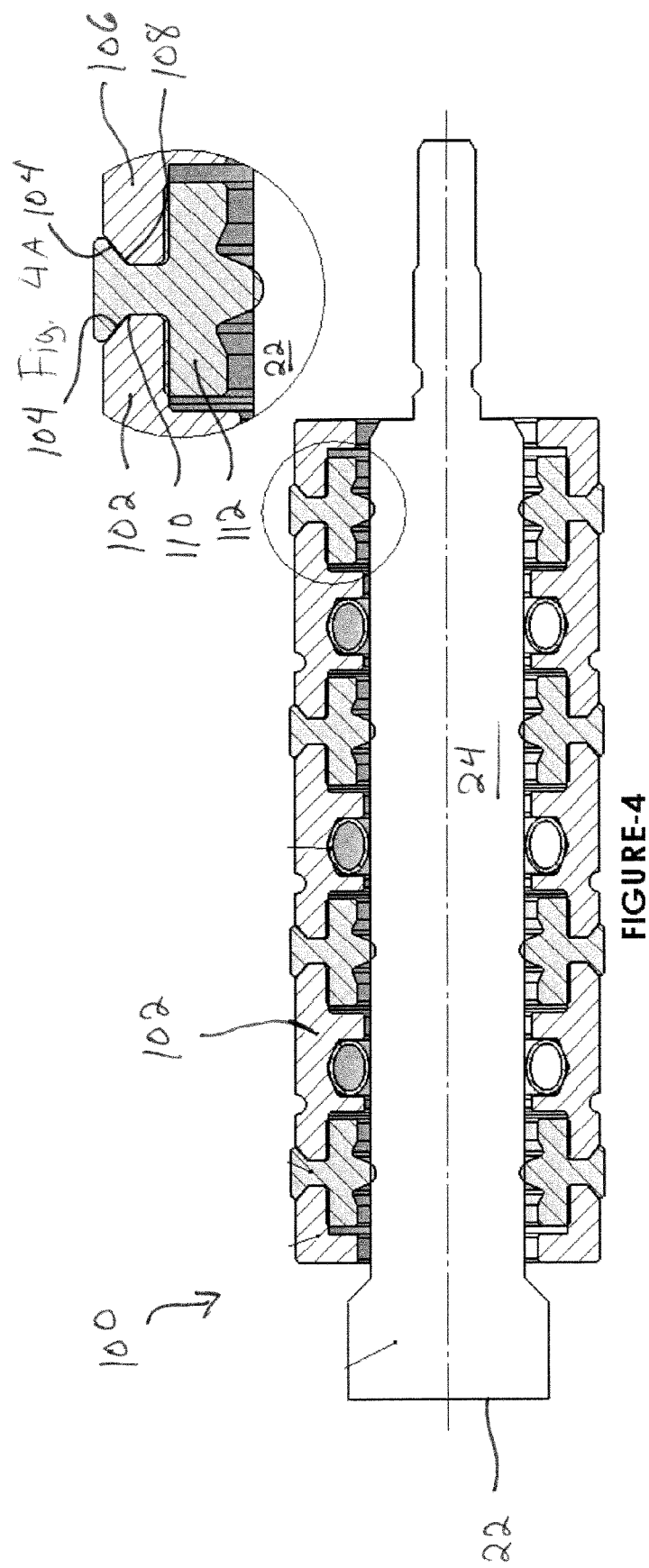
FIG. 4 is a front cross-sectional view of another embodiment of the present connector assembly for use with IMDs or alternatively for transmitting multiple signals in an electrical-related application.

With reference to FIG. 4, another alternative embodiment 100 resembles the embodiment 20 of FIG. 1, and provides the same advantages as the embodiment 20 of FIG. 1. However, the embodiment 100 of FIG. 4 also lengthens the electrical arc pathway between adjacent contact ring 102 as in the embodiments of FIGS. 2 and 3. With reference to FIG. 4A, each contact ring 102 includes a chamfer 104 at the outer side of its opposite ends. Each holding ring 106 also includes a chamfer 104 at the outer side of the end of its cylindrical portion. When the assembly 100 is assembled, adjacent chamfers 104 form substantially V-shaped grooves 108, albeit of a truncated or modified type, such as a two-dimensional funnel shape structure. The outwardly extending annular flange 110 of the seal ring 112 includes a complementary shape to seat within the groove 108 and also fill the space between the ends of adjacent contact rings 102, or adjacent contact rings 102 and holding rings 108. The flange 110 includes a constant thickness at its inner portion that then tapers out to a maximum thickness at its outer end. The maximum thickness provides a longer electrical arc pathway between adjacent contact rings 102, the advantages of which are discussed above with respect to the embodiment of FIG. 2. The tapering width of the flange 110 and the complementary shaped chamfers 104 also may enhance the sealing properties of the flange 110. Also, the flange 110 protrudes beyond the outer surfaces of the contact rings 102 to provide sealing against inner surfaces of a pre-molded header or a device housing, as discussed above.

Figure 5:
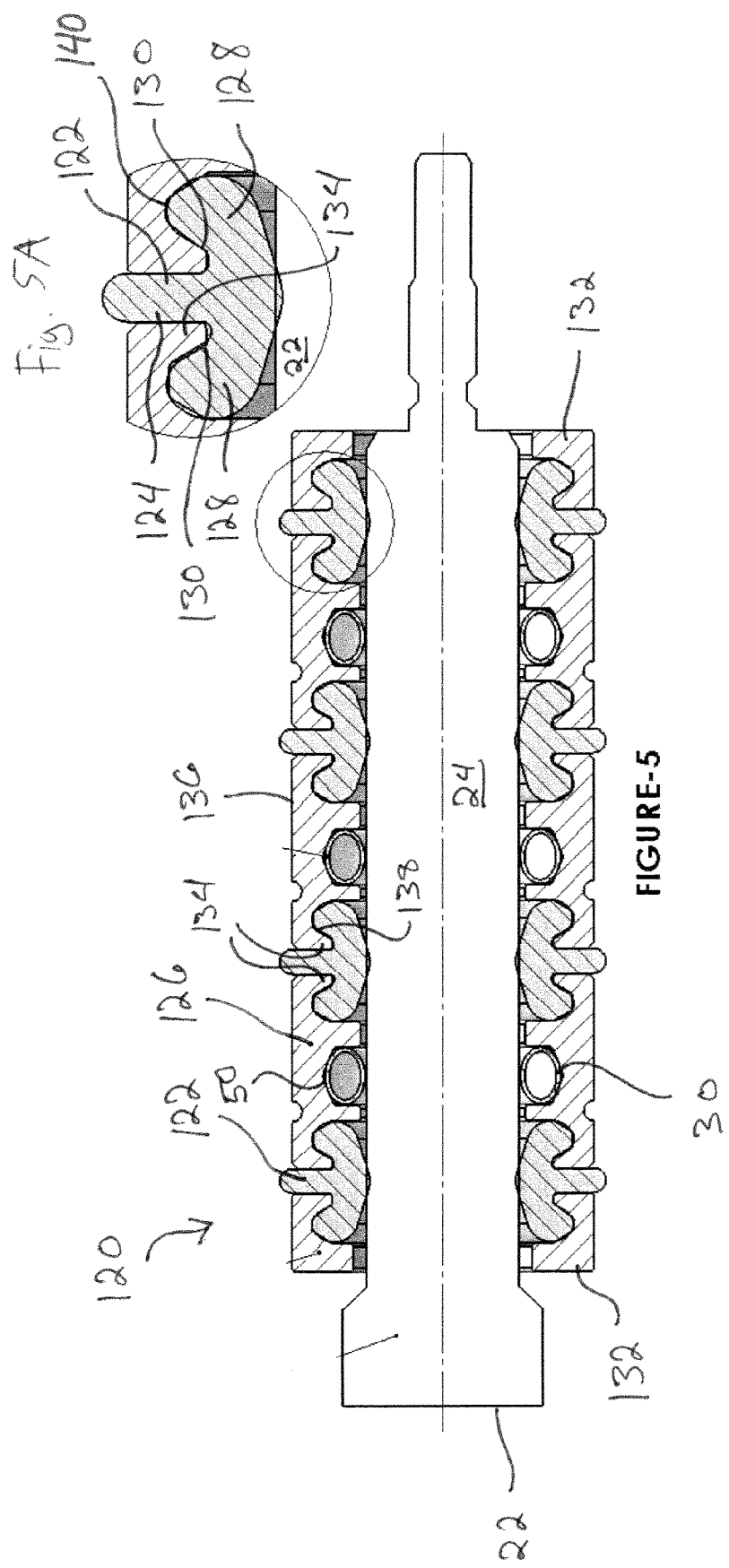
FIG. 5 is a front cross-sectional view of another embodiment of the present connector assembly for use with IMDs or alternatively for transmitting multiple signals in an electrical-related application.

FIG. 5 illustrates another alternative embodiment 120 of the present connector assemblies featuring interlocking of the contact rings 126 and the seal rings. With reference to FIG. 5A, a cross-sectional shape of each seal ring 122 resembles a T, with the particular view shown in FIG. 5A being an inverted T. A stem 124 of the T includes a constant width and seats between adjacent ends of the contact rings 126. The arms 128 of the T extend outward from the stem 124 but are also somewhat arc-shaped, curving outward and upward in the inverted T of FIG. 5A. The curved arms 128 thus form pockets 130 on either side of the stem 124. The pockets 130 receive interlocking portions of the contact rings 126 and holding rings 132, as discussed below.

With reference to FIG. 5. opposite ends of each contact ring 126 include a thickened portion 134. An outer surface 136 each contact ring 126 remains flat at either end. but an inner surface 138 slopes abruptly near the end to substantially increase the thickness of the contact ring 126 at its end. The increase in thickness creates a substantially U-shaped pocket 140 (FIG. 5A) that receives the seal ring 122. With reference to FIG. 5A, in the assembled state the seal ring 122 is located between adjacent contact rings 126, and between adjacent contact rings 126 and holding rings 132, such that the pockets 130 of the seal ring 122 receive the thickened ends 134 of the contact rings 126 and the pockets 130 of the contact rings 126 receive the branches 128 of the seal ring 122. The seal rings 122 and the contact rings 126 thus interlock in a structural engagement which resists axial movement of one seal ring from an adjacent contact ring. The interlocking of the seal rings 122 and the contact rings 126, as shown in FIGS. 5 and 5A, is by way of physical engagement or abutment between the thickened portion 134 of the seal ring and the U-shape pocket cup 140 of the contact ring. The structural engagement stabilizes the assembly 120 and hold it together during the assembly process. The interlocked components also provide tortuous interfaces that enhance the ability of the seal rings 122 to provide a liquid-tight seal against the contact rings 126.

The interlocking feature of the present embodiments provides numerous advantages. For example, the structural engagement of the interlocking, which is a snap fit engagement, resists separation of the contact rings 126 and the seal rings 122 from one another in the absence of applied compression. In other words, even without applied compression to hold the various components together, the components resist axial separation due to the structural engagement between the thickened portion 134 of the seal ring and the U-shape pocket cup 140 of the contact ring. The interlocking thus simplifies assembly. because the assembled components do not require any externally applied compression to hold them together. The interlocking also facilitates shipping of the assemblies 120, because there is no need to, for example, shrinkwrap the assembly 120 prior to packaging and shipping.

With further reference to FIG. 5A, a length of the stem 124 of each T-shaped seal ring 122 is greater than a wall thickness of the contact rings 126. An outer end of the stem 124 thus protrudes from the assembly 120. The stems 124 provide sealing against an inner surface of a pre-molded header assembly (not shown).

In one embodiment of a method of assembling the connector assembly of FIG. 5, the spring contacts 30 are first placed within the grooves 50 in the contact rings 126. A first holding ring 132 is then interlocked with a first seal ring 122 in coaxial alignment, followed by a first contact ring 126 interlocking with the first seal ring 122 in coaxial alignment. Successive seal rings 122 and contact rings 126 are then interlocked in coaxial alignment until a desired number of contact rings 126 have been added. A second holding ring 132 is then interlocked in coaxial alignment with the last added seal ring 122, opposite the first holding ring 132. In certain embodiments, the assembly process may be performed by hand without tools. The interlocking engagement of the components advantageously provides stability to the assembly as it is being assembled, retaining all components in coaxial alignment without the need for a dowel or assembly pin.

In another example, the connector assembly of FIG. 5 incorporates groves for receiving annular bands, similar to FIG. 2 or FIG. 3.

Figure 6:
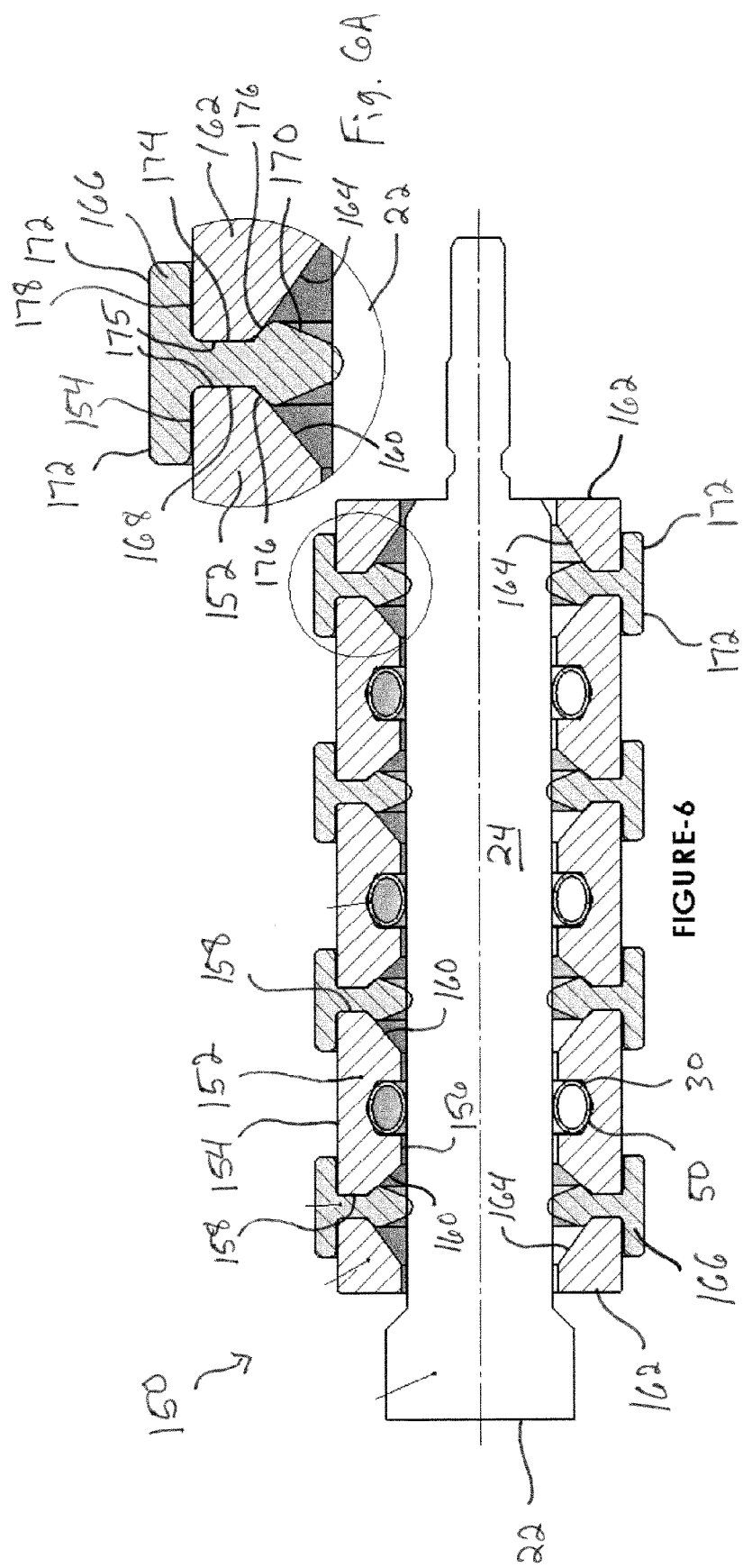
FIG. 6 is a front cross-sectional view of another embodiment of the present connector assembly for use with IMDs or alternatively for transmitting multiple signals in an electrical-related application.

FIG. 6 illustrates another alternative embodiment 150 of the present connector assemblies. A cross-sectional shape of each contact ring 152 resembles a trapezoid, with an outer surface 154 of the contact ring 152 forming a base 170 of the trapezoid and an inner surface 156 of the contact ring 152 forming a shorter parallel side of the trapezoid. Opposite ends 158 of the contact ring 152 form short parallel sides, and sloping sides 160 connect the ends 158 with the inner surface 156. An inner diameter of the contact ring 152 is large enough so that the contact rings 152 remain spaced from the electrical lead body 24. As shown, the sloping sides 160 are generally straight, i.e., having a constant slope, and terminate in generally straight end walls 158, which are generally perpendicular to the central axis of the connector assembly.

At or near its center, the inner surface 156 of the contact ring 152 includes a double-walled groove 50 having a V-shaped base 170. The groove 50 receives the spring contact element 30, which is preferably a garter-type radial or axial canted-coil spring. The relative sizes of the groove 50 and the spring 30 are as discussed above with respect to FIG. 1. Further, the double-walled groove 50 provides the same advantages as discussed above with respect to FIG. 1.

With continued reference to FIG. 6, each holding ring 162 is substantially cylindrical with a chamfer 164 at a corner that faces toward the interior of the assembly 150. The chamfer 164 provides a sloped surface that is complementary to the shape of the seal rings 166, as discussed further below. The holding rings 162 are sized so that they are spaced from the electrical lead 22.

With reference to FIG. 6A, the cross-section of each seal ring 166 is shaped substantially as a T. The stem 168 of the T extends between ends of adjacent contact rings 152, or between an end of a contact ring 152 and an adjacent holding ring 162, to provide a liquid-tight seal at the interfaces. A base 170 of the stem 168 includes a tapering width, forming an arrowhead shape that points away from the arms 172 of the T. The stem 168 thus forms a shape that is complementary to the gap between the ends of the adjacent contact rings 152, or between an end of a contact ring 152 and an adjacent holding ring 162. A constant width portion 174 of the stem 168 seats between facing parallel ends 175 of the contact rings 152/holding rings 162. Outwardly tapering sides 176 at the base 170 of the stem 168 seat against the sloping walls 160/164 of the contact rings 152/holding rings 162. From a location of maximum width, the stem 168 then tapers back inwardly, extending toward and abutting the lead cable 22 in an interference fit to provide a liquid-tight seal at the interface.

With reference to FIG. 6, the T of each seal ring 166 further includes oppositely extending arms 172 that abut the outer surfaces 154/178 of the adjacent contact rings 152/holding rings 162. An interference fit may be provided between the arms 172 and the outer surfaces 154/178 to enhance sealing. The T shape of each seal ring 166 advantageously provides sealing at multiple interfaces between the seal rings 166 and the contact rings 152/holding rings 162. For example, the arms 172 seal against the outer surfaces 154/178, and the stem 168 seals against the facing parallel surfaces 175 and the sloping surfaces 160/164. The substantial length of the interface between the seal rings 166 and the contact rings 152/holding rings 162 enhances sealing. The arms 172 of the T, being positioned outside the assembly 150, also are configured to provide sealing engagement with a pre-molded header (not shown).

With reference to FIG. 6A, the interlocking shapes of the stem 168 and the contact rings 152/holding rings 162 provide an additional advantage by stiffening the stem 168. The width of the stem 168 tapers outwardly from a point at the interface with the electrical lead 22 to a maximum width where the stem 168 contacts the sloped surfaces 160/164 of the contact rings 152/holding rings 162 and then inwardly again along the interface with the sloped surfaces 160/164. The sloped surfaces 160/164 provide abutment surfaces against which the tapered portions 176 of the stem 168 bear as the electrical lead 22 is inserted and withdrawn. The interference fit between the electrical lead 22 and the seal rings 166 urges the stems 168 of the seal rings 166 to flex in order to accommodate the electrical lead 22 as it is inserted. But abutment of the stems 168 against the sloped surfaces 160/164 of the contact rings 152/holding rings 162 resists flexing of the stems 168, thereby stiffening the seal rings 166. The stiffening enhances the sealing provided by the seal rings 166 by increasing the force with which the stems 168 bear against the electrical lead 22. The stiffening also increases the force necessary to withdraw the electrical lead 22 from the contact assembly 150, which reduces the likelihood of undesirable accidental withdrawal.

In one embodiment of a method of assembling the connector assembly 150 of FIG. 6, the spring contacts 30 are first placed within the grooves 50 in the contact rings 152. A first holding ring 162 is then engaged with a first seal ring 166 in coaxial alignment, followed by a first contact ring 152 engaging the first seal ring 166 in coaxial alignment. Successive seal rings 166 and contact rings 152 are then added in coaxial alignment until a desired number of contact rings 152 have been added. A second holding ring 162 is then engaged in coaxial alignment with the last added seal ring 166, opposite the first holding ring 162. In certain embodiments, the assembly process may be performed by hand without tools. Alternatively, a dowel or assembly pin (not shown) may be used. The dowel or pin first receives a holding ring 162, and then the other components are slid onto the pin and into engagement with the earlier placed components.

Thus, an aspect of the present assembly, device, and method is understood to include a connector comprising a plurality of alternating seal elements 166 and contact rings 152, wherein each contact ring comprises a groove defined by a side wall having an outside sloping surface; wherein each seal element comprises a stem and a base having a tapered surface; and wherein the tapered surface of the base contacts the sloping surface along a straight line.

Figure 7:
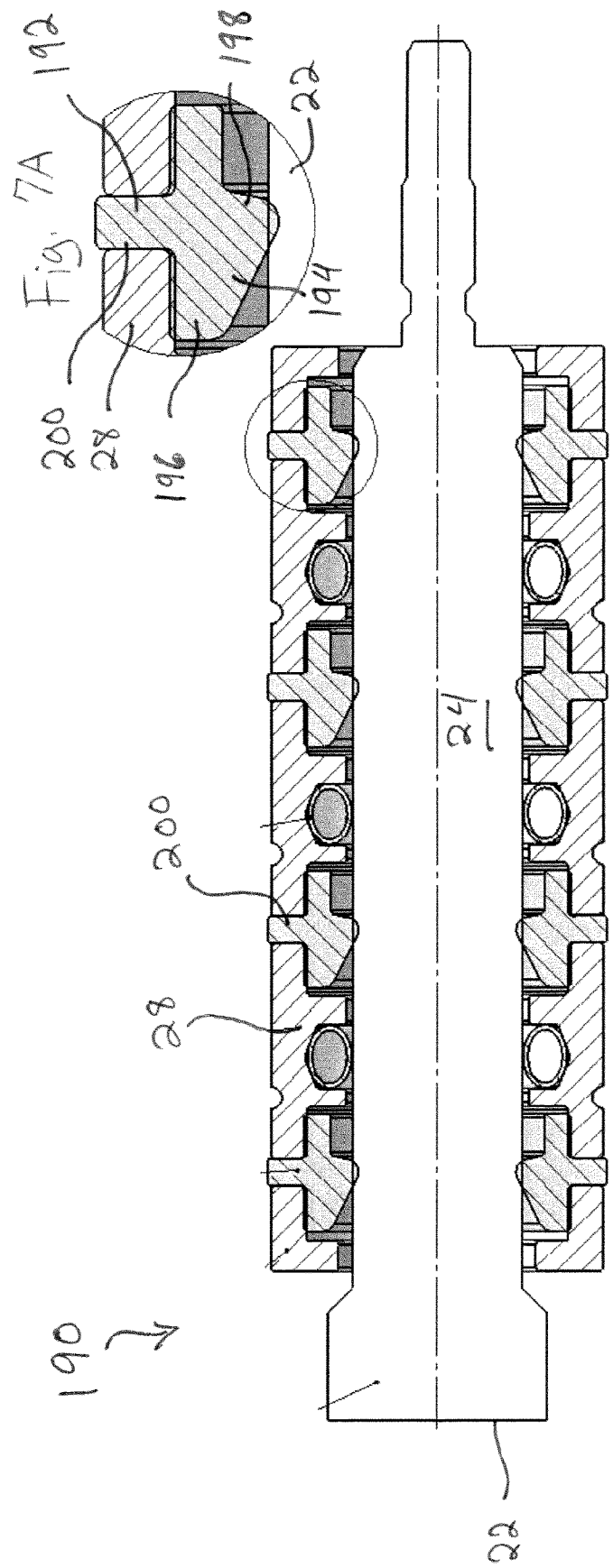
FIG. 7 is a front cross-sectional view of another embodiment of the present connector assembly for use with IMDs or alternatively for transmitting multiple signals in an electrical-related application.

FIG. 7 illustrates another alternative embodiment 190 of the present connector assemblies. The embodiment 190 of FIG. 7 is similar in configuration to the embodiment 20 of FIG. 1, except with respect to the cross-sectional shape of the seal rings 192. In comparison with the seal ring 26 of FIG. 1A, the seal ring 192 of FIG. 7A eliminates the cutouts 42 (FIG. 1A) and adds additional material 194 (FIG. 7A) in the region between the proximally extending arm 196 and the inwardly extending annular flange 198. The seal rings 192 thus include a non-symmetrical shape. As used herein, the terms proximal and distal are used with reference to a direction of insertion of the electrical lead 22. In FIG. 7 the electrical lead 22 is inserted through the left-hand side, or proximal side, of the assembly 190.

Because the seal ring 192 includes more material 194 on its proximal side than on its distal side, the inwardly extending annular flange 198 may deflect more easily in the distal direction than in the proximal direction. The shape of the seal ring 192 thus creates unequal insertion and removal forces for the electrical lead 22. When the electrical lead 22 is inserted, it moves from left to right in FIG. 7, deflecting the flanges 198 distally. When the electrical lead 22 is removed, it moves from right to left in FIG. 7, deflecting the flanges 198 proximally. Because the flanges 198 deflect more easily in the distal direction than in the proximal direction, the removal force is greater than the insertion force. The connector assembly thus advantageously facilitates insertion of the electrical lead 22 during manufacture, and resists accidental withdrawal of the electrical lead 22 after manufacture.

Thus, an aspect of the present assembly, device, and method is understood to include a connector comprising a plurality of alternating seal elements 192 and contact elements 28, wherein each seal element has a non-symmetrical cross-section for modifying an insertion force versus a removal force of a lead cable. In one embodiment, the insertion force is less than the removal force. In another embodiment, the insertion force is greater than the removal force.

With further reference to FIG. 7A, a length of the outwardly extending annular flange 200 of each seal ring 192 is greater than a wall thickness of the contact rings 28. An outer end of the flange 200 thus protrudes from the assembly 190. The flanges 200 provide sealing against an inner surface of a pre-molded header assembly (not shown).

Figure 8:
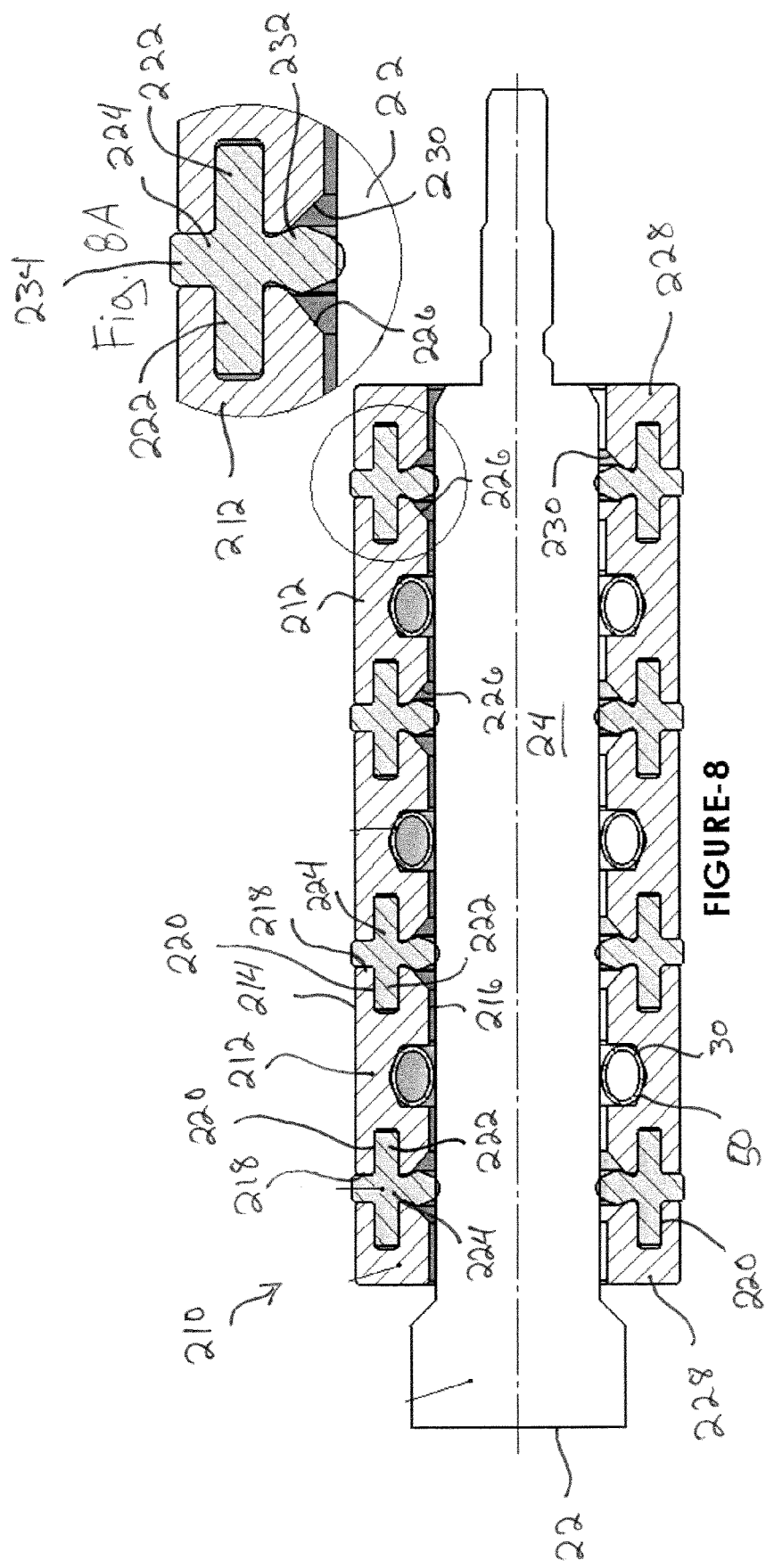
FIG. 8 is a front cross-sectional view of another embodiment of the present connector assembly for use with IMDs or alternatively for transmitting multiple signals in an electrical-related application.

FIG. 8 illustrates another alternative embodiment 210 of the present connector assemblies. Each contact ring 212 includes a smooth cylindrical outer surface 214, a smooth cylindrical inner surface 216 including a central groove 50, and opposite end surfaces 218 including axially extending grooves 220. An inner diameter of each contact ring 212 is large enough so that the contact rings 212 remain spaced from the electrical lead 22 body 24.

The groove 50 in the inner surface of the contact ring 212 is double walled and includes a V-shaped base. The groove 50 receives the spring contact element 30, which is preferably a garter-type radial or axial canted-coil spring. The relative sizes of the groove 50 and the spring 30 are as discussed above with respect to FIG. 1. Further, the double-walled groove 50 provides the same advantages as discussed above with respect to FIG. 1.

With continued reference to FIG. 8, the opposite end surfaces 218 of the contact ring 212 include axially extending grooves 220, which extend co-axially with the central axis of the common bore. In the illustrated embodiment, a cross-section of each groove 220 is substantially rectangular. The grooves 220 could, however, have any shape. The grooves 220 are configured to receive flanges 222 of the seal rings 224, as described further below.

At opposite ends of the inner surface 216, each contact ring 212 includes a chamfer forming a sloped surface 226. The sloped surfaces 226 are configured to engage the seal rings 224, as described further below.

With continued reference to FIG. 8, each holding ring 228 is substantially cylindrical with a chamfer 230 at a corner that faces toward the interior of the assembly 210. The chamfer 230 provides a sloped surface that is complementary to the shape of the seal rings 224, as discussed further below. Each holding ring 228 further includes a groove 220 in a surface that faces the adjacent contact ring 212. The groove 220 is sized and shaped similarly to the grooves 220 in the end surfaces of the contact rings 212, and is also configured to receive a flange 222 of one of the seal rings 224, as described further below. The holding rings 228 are sized so that they are spaced from the electrical lead 22.

With reference to FIG. 8A, the cross-section of each seal ring 224 is shaped substantially as a cross. Each seal ring 224 includes an inwardly extending annular flange 232 that is configured to abut the lead cable 22 in an interference fit to provide a liquid-tight seal at the interface. Similar to the embodiment of FIG. 6, the inwardly extending annular flange 232 includes a tapering width forming a teardrop shape. The teardrop shaped flange 232 seats between adjacent sloped surfaces 226/230 on the contact rings 212/holding rings 228. Engagement between the teardrop shaped flange and the sloped surfaces 226/230 creates the stiffening effect discussed above with respect to the embodiment of FIG. 6.

With continued reference to FIG. 8A, each seal ring 224 further includes an outwardly extending annular flange 234 that is configured to seat between and abut adjacent contact rings 212 in a liquid-tight seal at each interface. An outer end of each outwardly extending annular flange 234 protrudes from the assembly 210. The protruding flanges 234 are configured to bear against an inner surface of a pre-molded header assembly (not shown) in a liquid tight seal at the interface.

Each seal ring 224 further includes annular flanges 222 that extend in opposite longitudinal directions. In the cross-sectional view of FIG. 8A, the flanges 222 resemble arms of the cross. Each flange 222 has a rectangular cross-section, and is sized to matingly fit within one of the grooves 220 in the contact rings 212/holding rings 228. The flanges 222 and the grooves 220 thus interlock the contact rings 212 and the seal rings 224, with the flanges 222 providing a liquid-tight seal at the interfaces. An interference fit may be provided between the flanges 222 and the grooves 220 to enhance interlocking and sealing. As in previous embodiments, sealing advantageously occurs at multiple interfaces between the seal rings 224 and the contact rings 212. Further, the lengthy and tortuous liquid path from the exterior of the assembly 210 to the interior of the assembly 210 resists intrusion of bodily fluids into the connector assembly and into the can. In the embodiment of FIG. 8, the flanges 222 and the grooves 220 increase the length of the liquid path from the exterior of the assembly 210 to the interior of the assembly 210 without affecting the spacing between adjacent contact rings 212. To further enhance sealing, the depths of the grooves 220 and the widths of the flanges 222 can be increased, again without affecting the spacing between adjacent contact rings 212.

In one embodiment of a method of assembling the connector assembly 210 of FIG. 8, the spring contacts 30 are first placed within the grooves 50 in the contact rings 212. A first holding ring 228 is then interlocked with a first seal ring 224 in coaxial alignment with a first flange 222 of the seal ring 224 seated within the groove 220 in the holding ring 228. A first contact ring 212 is then interlocked with the first seal ring 224 in coaxial alignment with a second flange 222 of the seal ring 224 seated within the groove 220 in the contact ring 212. Successive seal rings 224 and contact rings 212 are then added in interlocking coaxial alignment until a desired number of contact rings 212 have been added. A second holding ring 228 is then interlocked in coaxial alignment with the last added seal ring 224, opposite the first holding ring 228. In certain embodiments, the assembly process may be performed by hand without tools. The interlocking engagement of the components advantageously provides stability to the assembly as it is being assembled, retaining all components in coaxial alignment without the need for a dowel or assembly pin. However, in alternative assembly methods a dowel or assembly pin (not shown) may be used. The dowel or pin first receives a holding ring 228, and then the other components are slid onto the pin and into engagement with the earlier placed components.

Figure 9:
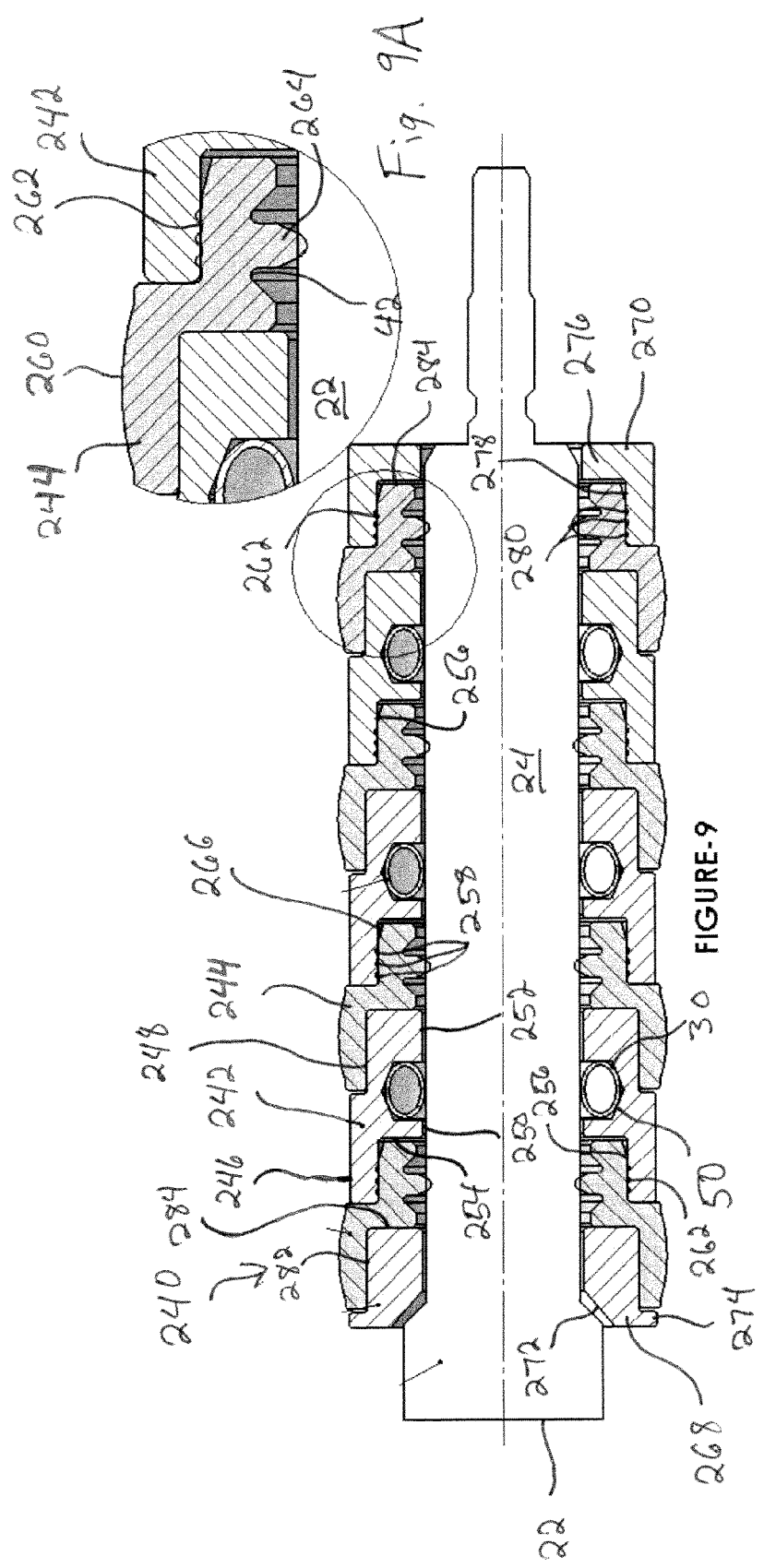
FIG. 9 is a front cross-sectional view of another embodiment of the present connector assembly for use with IMDs or alternatively for transmitting multiple signals in an electrical-related application.

FIG. 9 illustrates another alternative embodiment 240 of the present connector assemblies in which the contact rings 242 and the seal rings 244 are shaped as overlapping stepped cylinders. In particular, each contact ring 242 includes a stepped outer surface comprising a first smooth cylindrical surface 246 forming a first greater outer diameter and a second smooth cylindrical surface 248 forming a second lesser outer diameter. Each contact ring 242 further includes first and second spaced annular flanges 250, 252 that extend inwardly. Inner diameters of the flanges 250, 252 are large enough so that the contact rings 242 remain spaced from the electrical lead body 24. The flanges 250, 252 form a double-walled groove 50 having a V-shaped bottom. The groove 50 receives the spring contact element 30, which is preferably a garter-type radial or axial canted-coil spring. The relative sizes of the groove 50 and the spring 30 are as discussed above with respect to FIG. 1. Further, the double-walled groove 50 provides the same advantages as discussed above with respect to FIG. 1.

In the illustrated embodiment, each of the first flanges 250 has a first narrower width and each of the second flanges 252 has a second wider width. Adjacent the first flange 250 and opposite the groove 50, each contact ring 242 includes an undercut 254 that receives a portion of the seal ring 244, as described below. An inner surface 256 of the contact ring 242 in the region of the undercut 254 includes spaced annular grooves 258 that contribute to interlocking the contact rings 242 with the seal rings 244 by enabling the softer material of the seal ring 244 to deform into the grooves 258 and form interlocking ridges. Three grooves 258 are shown, but any number could be provided.

With reference to FIG. 9A, each seal ring 244 includes a stepped outer surface comprising a first cylindrical surface 260 forming a first greater outer diameter and a second cylindrical surface 262 forming a second lesser outer diameter. The first outer surface 260 is convex to enhance sealing against inner surfaces of a pre-molded header, as described above with respect to the annular bands 68 of FIG. 2. Each seal ring 244 further includes an inwardly extending annular flange 264 opposite the second outer surface 262. The flange 264 is configured to abut the lead cable 22 in an interference fit to provide a liquid-tight seal at the interface. Undercuts 42 on opposite sides of the flange 264 provide the same advantages as described above with respect to the embodiment of FIG. 1. An end of the second outer surface 262 includes a chamfer 266 that facilitates assembly of the contact rings 242 and seal rings 244, as described below.

The assembly further includes first and second holding rings 268, 270, which in contrast to previous embodiments are not symmetrical. The first holding ring 268 is cylindrical and includes a chamfer 272 at an inner, proximal edge. The chamfer 272 facilitates insertion of the electrical lead 22 by guiding the lead 22 toward the interior of the assembly 240. The first holding ring 268 further includes an outwardly extending flange 274 at a proximal end. The second holding ring 270 is cylindrical and includes an inwardly extending flange 276 at a distal end. An inner surface 278 of the second holding ring 270 includes spaced annular grooves 280 that contribute to interlocking the second holding ring 270 with its adjacent seal ring 244 by enabling the softer material of the seal ring 244 to deform into the grooves 280 and form interlocking ridges. Three grooves 280 are shown, but any number could be provided.

In the assembled connector assembly, the contact rings 242 and the seal rings 244 alternatingly overlap one another along the length of the assembly 240. The outer surface of the assembly thus comprises alternating bands of the contact rings 242 and the seal rings 244. The alternating bands may be described as cylinders extending along the outer surface of the assembly 240.

With reference to the proximal (left) side of FIG. 9, the undercut 254 in the contact ring 242 receives the seal ring 244 such that the inner surface 256 of the contact ring 242 abuts the second outer surface 262 of the seal ring 244. The seal ring 244 provides a liquid tight seal at the interfaces. The annular grooves 258 in the contact ring 242 provide grip against the seal ring 244 to enhance the interlocking fit. An interference fit may be provided to further enhance sealing and interlocking.

With continued reference to the proximal (left) side of FIG. 9, and just distally of the first contact ring 242, the seal ring 244 overlaps the contact ring 242 and abuts the second outer surface 248 and the second flange 252 of the contact ring 242. Again, the seal ring 244 provides a liquid tight seal at the interfaces. An interference fit may be provided to further enhance sealing and interlocking.

With continued reference to the proximal (left) side of FIG. 9, the most proximal seal ring 244 receives the first holding ring 268. The seal ring 244 overlaps the outer surface 282 of the first holding ring 268 and abuts the distal surface 284 thereof. Again, the seal ring 244 provides a liquid tight seal at the interfaces. An interference tit may be provided to further enhance sealing and interlocking.

With reference to the distal (right) side of FIG. 9, the second holding ring 270 receives the most distal seal ring 244. The second holding ring 270 overlaps the second outer surface 262 of the seal ring 244, and may abut the distal surface 284 thereof. Again, the seal ring 244 provides a liquid tight seal at the interfaces. The annular grooves 280 in the second holding ring 270 provide grip against the seal ring 244 to enhance the interlocking fit. An interference fit may be provided to further enhance sealing and interlocking.

In one embodiment of a method of assembling the connector assembly 240 of FIG. 9, the spring contacts 30 are first placed within the grooves 50 in the contact rings 242. The first holding ring 268 is then interlocked with a first seal ring 244 in coaxial alignment with the seal ring 244 overlapping the holding ring 268. A first contact ring 242 is then interlocked with the first seal ring 244 in coaxial alignment with the contact ring 242 overlapping the seal ring 244. The chamfer 266 at the distal outer edge of the seal ring 244 facilitates overlapping the contact ring 242 with the seal ring 244. Successive seal rings 244 and contact rings 242 are then added in interlocking coaxial alignment until a desired number of contact rings 242 have been added. Each time a new ring is added, it overlaps the previously added ring. A second holding ring 270 is then interlocked in coaxial alignment with the last added seal ring 244, opposite the first holding ring 268, with the second holding ring 270 overlapping the seal ring 244. In certain embodiments, the assembly process may be performed by hand without tools. The interlocking engagement of the components advantageously provides stability to the assembly as it is being assembled, retaining all components in coaxial alignment without the need for a dowel or assembly pin. However, in alternative assembly methods a dowel or assembly pin (not shown) may be used. The dowel or pin first receives a holding ring 268, and then the other components are slid onto the pin and into engagement with the earlier placed components.

Figure 10:
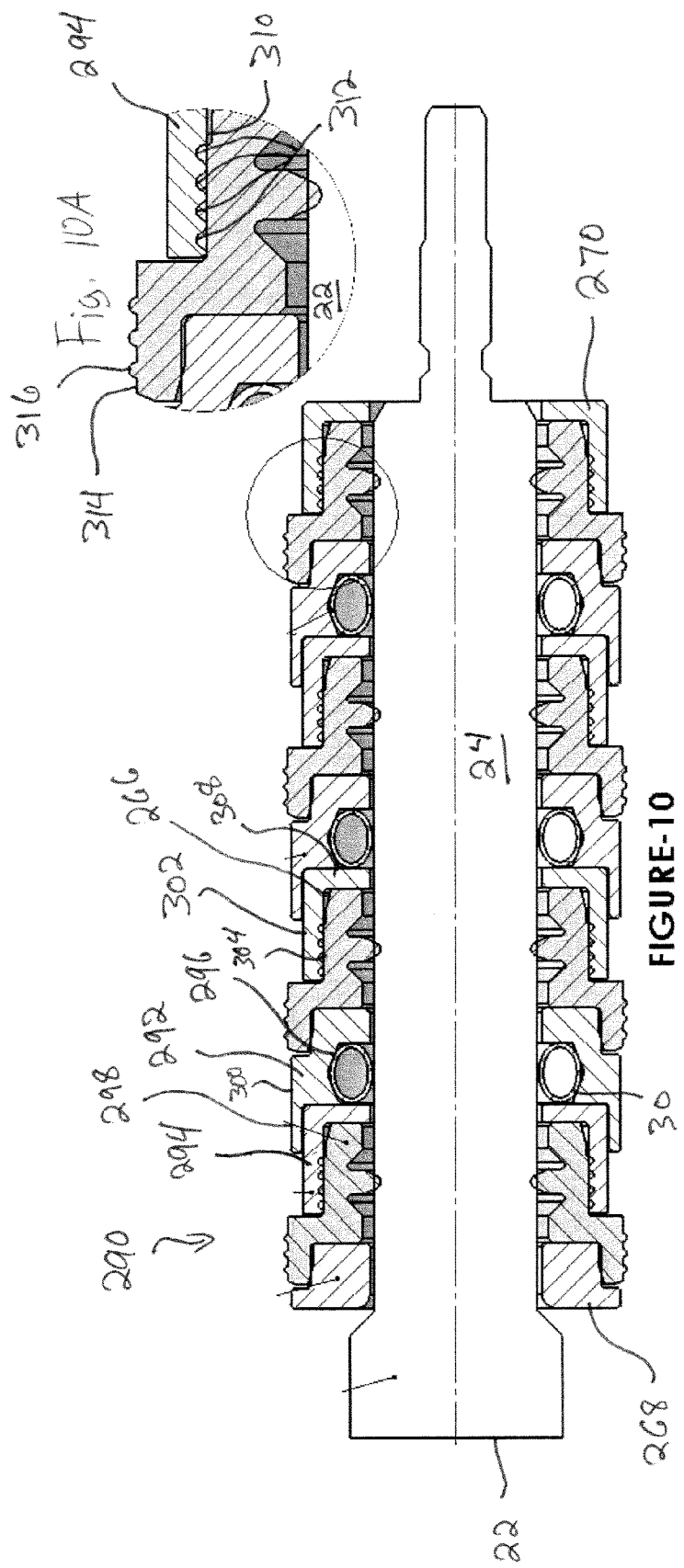
FIG. 10 is a front cross-sectional view of another embodiment of the present connector assembly for use with IMDs or alternatively for transmitting multiple signals in an electrical-related application.

FIG. 10 illustrates another alternative embodiment 290 of the present connector assemblies. The embodiment 290 of FIG. 10 is similar in configuration to the embodiment 240 of FIG. 9. However, the embodiment 290 of FIG. 10 reshapes the contact rings 292 and adds spacers 294. A distal portion of each contact ring 292 remains unchanged from the embodiment 240 of FIG. 9. However, the portion of the contact ring 292 proximal of the groove 296 is removed except for a flange 298 that extends proximally at the outer surface 300 of the contact ring 292. The contact ring 292 thus includes a single-walled groove 296, as opposed to the double-walled grooves 50 of the previous embodiments, for receiving the spring contact 30, as described below.

In the embodiment of FIG. 10, a spacer 294 replaces the portion of the contact ring 292 that has been removed when compared to the embodiment 240 of FIG. 9. Each spacer 294 is L-shaped, with a spine 302 of the L extending in the proximal direction and seating between the outer flange 298 of the contact ring 292 and the second outer surface 304 of the seal ring 306. A base 308 of the L extends radially inward at the distal end of the flange 298, seating between the contact ring 292 and the seal ring 306 and forming a second sidewall for the spring groove 296. With reference to FIG. 10A, the inner surface 310 of the spine 302 of the L includes spaced annular grooves 312 that contribute to interlocking the spacer 294 with the seal rings 306, as described above with respect to the embodiment 240 of FIG. 9. Three grooves 312 are shown, but any number could be provided.

The single-walled groove 296 in each contact ring 292 facilitates assembly. The previous embodiments include a double-walled groove 50 having an annular shape. Thus, to combine the annular canted-coil spring 30 with the contact ring 242, the spring 30 must be inserted from the interior of the contact ring 242 where the opening in the groove 50 is located. Because the spring 30 is sized to seat within the groove 50, inserting it from within the contact ring 242 requires that the spring 30 be deformed. This process presents challenges, such as being difficult to automate. With the single-walled groove 296 of the contact ring 292 of FIG. 10, the spring 30 can be inserted into the groove 296 in the longitudinal direction from the open side. This process is much less challenging, as it requires far less deformation of the spring 30. The embodiment of FIG. 10 is thus easier to assemble.

With reference to FIG. 10A, the embodiment 290 of FIG. 10 further differs from the embodiment 240 of FIG. 9 in that the first outer surface 314 of each seal ring 306 includes a plurality of spaced, annular, raised ridges 316. Three ridges 316 are shown, but any number could be provided. The ridges 316 enhance the ability of the seal ring 306 to seal against the inner surfaces of a pre-molded header (not shown).

The spacer 294 may be made from the same material as the contact rings 292. Alternatively, the spacer 294 may be made from an implantable-grade, electrically non-conductive, rigid plastic material, such as PolyEtherEtherKetone (PEEK).

In one embodiment of a method of assembling the connector assembly of FIG. 10, the spring contacts 30 are first placed within the grooves 296 in the contact rings 292. As indicated above, this step can be performed quite easily by inserting the spring 30 into the groove 296 in the longitudinal direction from the open side. The first holding ring 268 is then interlocked with a first seal ring 306 in coaxial alignment with the seal ring 306 overlapping the holding ring 268. A first spacer 294 is then interlocked with the first seal ring 306 in coaxial alignment with the first spacer 294 overlapping the seal ring 306. The chamfer 266 at the distal outer edge of the seal ring 306 facilitates overlapping the spacer 294 with the seal ring 306. A first contact ring 292 is then interlocked with the first spacer 294 in coaxial alignment with the contact ring 292 overlapping the first spacer 294. Successive seal rings 306, spacers 294 and contact rings 292 are then added in interlocking coaxial alignment until a desired number of contact rings 292 have been added. Each time a new ring or spacer is added, it overlaps the previously added ring or spacer. A second holding ring 270 is then interlocked in coaxial alignment with the last added seal ring 306, opposite the first holding ring 268, with the second holding ring 270 overlapping the seal ring 306. In certain embodiments, the assembly process may be performed by hand without tools. The interlocking engagement of the components advantageously provides stability to the assembly as it is being assembled, retaining all components in coaxial alignment without the need for a dowel or assembly pin. However, in alternative assembly methods, a dowel or assembly pin (not shown) may be used. The dowel or pin first receives a holding ring, and then the other components are slid onto the pin and into engagement with the earlier placed components.

Figure 11:
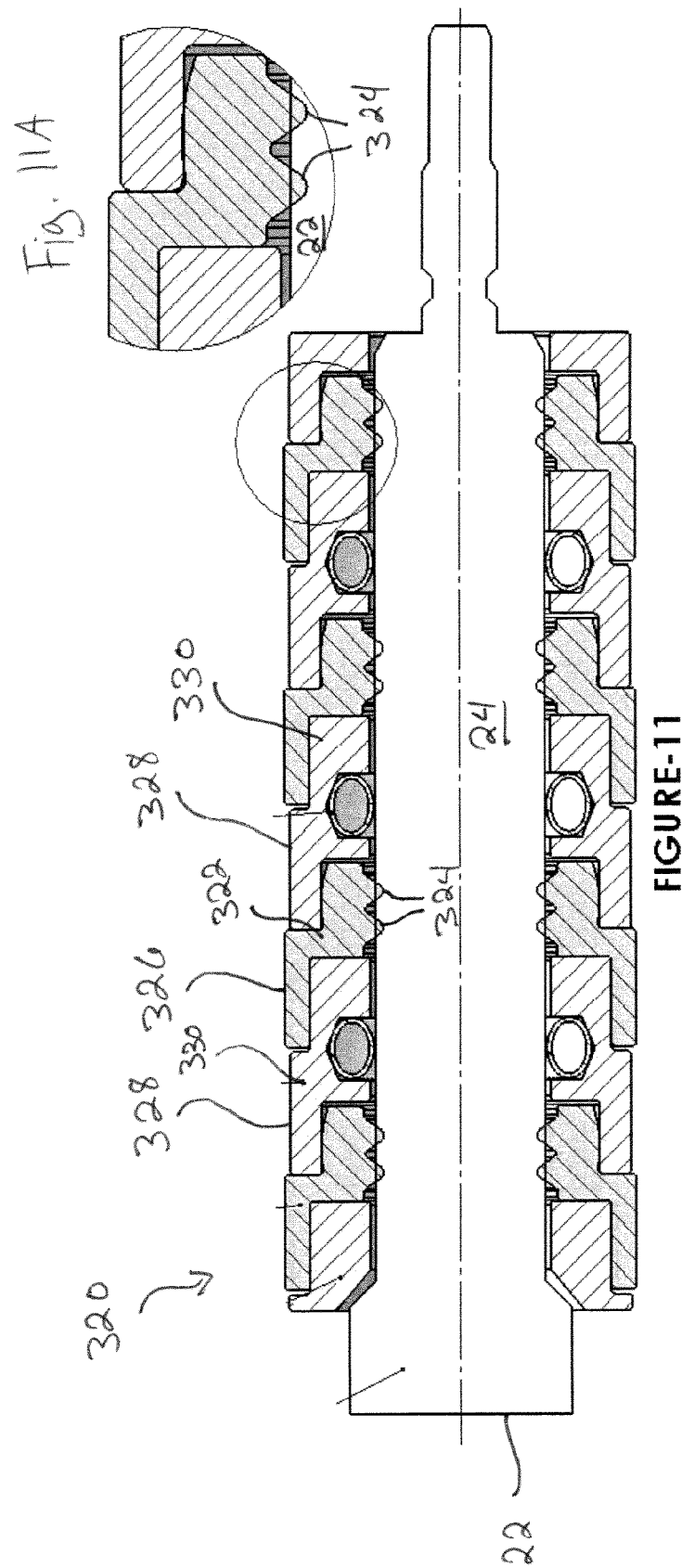
FIG. 11 is a front cross-sectional view of another embodiment of the present connector assembly for use with IMDs or alternatively for transmitting multiple signals in an electrical-related application.

FIG. 11 illustrates another alternative embodiment 320 of the present connector assemblies. The embodiment 320 of FIG. 11 is similar in configuration to the embodiment 240 of FIG. 9. However, the embodiment 320 of FIG. 11 includes a seal ring 322 having a double lip seal. With reference to FIG. 9, the seal ring 244 includes a single inwardly extending annular flange 264 that forms a seal with the lead body 24. With reference to FIG. 11, the seal ring 322 includes two spaced inwardly extending annular flanges 324 that form a double lip seal with the lead body 24. The double lip seal enhances sealing around the lead body 24.

With further reference to FIG. 11, the seal ring 322 also includes a flat first outer surface 326, in contrast to the convex first outer surface 260 of the seal ring 244 of FIG. 9. The first outer surface 326, however, still protrudes beyond the adjacent first outer surfaces 328 of the contact ring 330 to provide for sealing contact with inner surfaces of a pre-molded header (not shown). In the embodiment of FIG. 11 the contact rings 330 also lack the spaced annular grooves 258 that are shown in FIG. 9.

Figure 12:
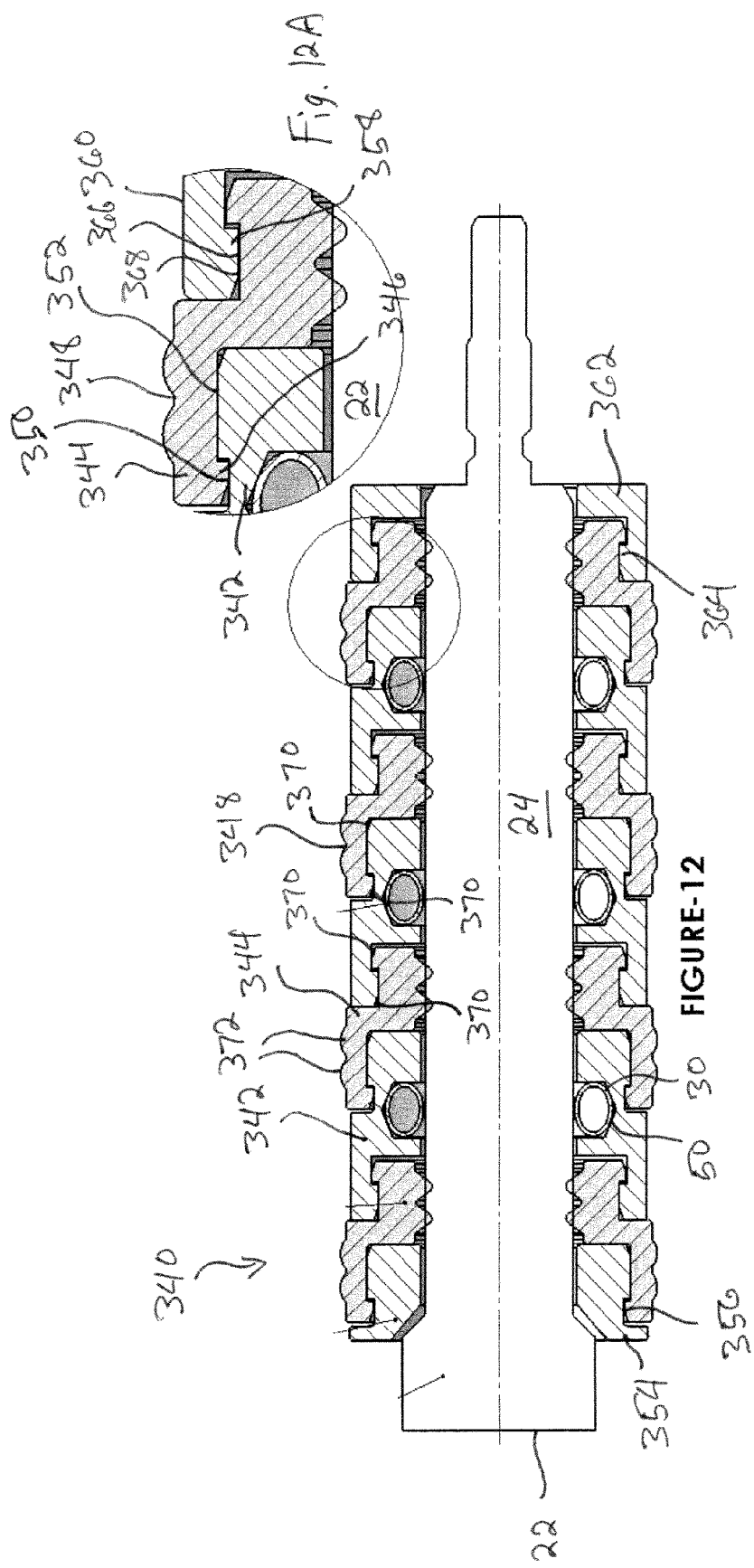
FIG. 12 is a front cross-sectional view of another embodiment of the present connector assembly for use with IMDs or alternatively for transmitting multiple signals in an electrical-related application.

FIG. 12 illustrates another alternative embodiment 340 of the present connector assemblies. The embodiment 340 of FIG. 12 is similar in configuration to the embodiment 320 of FIG. 11. However, in the embodiment 340 of FIG. 12 the contact rings 342 and seal rings 344 include interlocking features. With reference to FIG. 12A. each seal ring 344 includes a small flange 346 that extends inwardly from its proximal end opposite the first outer surface 348.

Each contact ring 342 includes a mating groove 350 at the proximal end of its second outer surface 352. The first holding ring 354 includes a similar groove 356 (FIG. 12). With further reference to FIG. 12A. each contact ring 342 includes a small flange 358 that extends inwardly from its proximal end opposite the first outer surface 360. The second holding ring 362 includes a similar flange 364 (FIG. 12). Each seal ring 344 includes a mating groove 366 at the proximal end of its second outer surface 368. Engagement of the flanges 346, 358 within the grooves 350, 366 enhances sealing at the interfaces and interlocks the seal rings 344 with the contact rings 342 and the seal rings 344 with the holding rings 354, 362. Thus. the contact rings 342 and the seal rings 344 interlock in a structural engagement which resists axial movement of one seal ring from an adjacent contact ring. The contact rings 352 and the holding rings 354, 362 are also interlocked by a similar structural engagement which resists axial movement of one contact ring from an adjacent holding ring. The physical structures of the flanges 346, 358 and the grooves 350, 366 resist axial separation to provide stability, ease of assembly without a dowel or assembly pin, and without external compressive force. The interlocking provides the same advantages as discussed above.

With reference to FIG. 12, both the contact rings 342 and the seal rings 344 include chamfers 370 at both their proximal and distal ends. The chamfers 370 provide ramped surfaces that urge the seal rings 344 to expand or contract as one ring 342, 344, 354, 362 is slid over another during assembly, as discussed further below.

The seal rings 344 of FIG. 12 also include spaced, annular, raised ridges 372 on their first outer surfaces 348. Two ridges 372 are shown, but any number could be provided. The ridges 372 enhance the ability of the seal ring 344 to seal against the inner surfaces of a pre-molded header (not shown).

In one embodiment of a method of assembling the connector assembly 340 of FIG. 12, the spring contacts 30 are first placed within the grooves 50 in the contact rings 342. The first holding ring 354 is then interlocked with a first seal ring 344 in coaxial alignment with the seal ring 344 overlapping the holding ring 354. To overlap the seal ring 344 with the holding ring 354, the chamfer 370 at the proximal end of the seal ring 344 is placed against the chamfer 370 at the distal end of the holding ring 354. Compression is then applied to force the seal ring 344 to expand and ride up over the holding ring 354 until the flange 346 snaps into the groove 356 in interlocking engagement. A first contact ring 342 is then interlocked with the first seal ring 344 in coaxial alignment with the contact ring 342 overlapping the seal ring 344. To overlap the contact ring 342 with the seal ring 344, the chamfer 370 at the proximal end of the contact ring 342 is placed against the chamfer 370 at the distal end of the seal ring 344. Compression is then applied to force the seal ring 344 to contract and ride underneath the contact ring 342 until the flange 358 snaps into the groove 366 in interlocking engagement which resists axial movement of one seal ring from an adjacent contact ring. Successive seal rings 344 and contact rings 342 are then added in interlocking coaxial alignment until a desired number of contact rings 342 have been added. The interlocking is a snap fit engagement, which is a physical engagement.

Each time a new ring is added, it overlaps the previously added ring with the flange 346, 358 snapping into the groove 350, 366. A second holding ring 362 is then interlocked in coaxial alignment with the last added seal ring 344, opposite the first holding ring 354, with the second holding ring 362 overlapping the seal ring 344. The flange 364 on the second holding ring 362 snaps into the groove 366 on the last added seal ring 344 in interlocking engagement. Thus, the interlocking of the components is a structural engagement which resists axial movement of one component from an adjacent component. In certain embodiments, the assembly process may be performed by hand without tools. The interlocking engagement of the components advantageously provides stability to the assembly as it is being assembled, retaining all components in coaxial alignment without the need for a dowel or assembly pin. However, in alternative assembly methods, a dowel or assembly pin (not shown) may be used. The dowel or ,pin first receives a holding ring, and then the other components are slid onto the pin and into engagement with the earlier placed components.

FIG. 13 illustrates another alternative embodiment 380 of the present connector assemblies. Each seal ring 382 is shaped as an annulus having a smooth outer surface 384. A pair of spaced annular flanges 384 extends inwardly from an inner surface of the seal ring 382. Although two flanges 384 are shown, any number could be provided. The flanges 384 are configured to abut the lead cable 22 in an interference fit to provide a liquid-tight seal at the interface. End surfaces 386 of the seal ring 382 are flat and parallel. The end surfaces 386 abut adjacent contact rings 388 and holding rings 390 in a liquid-tight seal at each interface.

Each of the holding rings 390 is cylindrical and includes an outwardly extending flange 392. For the proximal holding ring 390, the flange 392 is located at its distal end, and for the distal holding ring 390 the flange 392 is located at its proximal end. The holding rings 390 abut end surfaces 386 of the seal rings 382 at either end of the assembly 380.

Each contact ring 388 includes a stepped outer surface having a maximum diameter at a center portion 394 and smaller diameter portions 396 to either side of the center portion 394. Each of the smaller diameter portions 396 includes an annular groove 398 at the base of the center portion 394. End surfaces 400 of the contact ring 388 are flat and parallel and abut end surfaces 386 of the adjacent seal rings 382. An inner surface 402 of the contact ring 388 includes a double-walled groove 50 having a V-shaped bottom. The groove 50 receives the spring contact element 30, which is preferably a garter-type radial or axial canted-coil spring.

With further reference to FIG. 13, the assembly 380 further comprises a plurality of insulating rings 404. Each ring 404 is cylindrical and includes a smooth outer surface 406, a smooth inner surface 408, and first and second inwardly extending flanges 410 at opposite ends. The insulating rings 404 extend around the seal rings 382, with each seal ring 382 being generally centered within a respective insulating ring 404. The outer surface 384 of the seal ring 382 provides a liquid tight seal at the interface with the inner surface 408 of the insulating ring 404. The insulating rings 404 may engage the seal rings 382 in an interference fit to enhance sealing.

With reference to FIG. 13A, the flanges 410 at either end of the insulating rings 404 seat within the grooves 398 in the contact rings 388 in interlocking engagement, as shown in FIG. 13A. The flanges 410 on the insulating rings 404 also interlock with the flanges 392 on the holding rings 390 (FIG. 13). The flanges 410 include chamfers 412 on oppositely facing surfaces. The contact rings 388 similarly include chamfers 412 on oppositely facing surfaces. The flanges 392 on the holding rings 390 also include chamfers 412. The chamfers 412 urge the insulating rings 404 to expand as the insulating rings 404 are forced onto the contact rings 388 and the holding rings 390 under compression during assembly, as described above with respect to FIG. 12.

The insulating rings 404 provide interlocking structural support to the assembly 340, securing the holding rings 390 to the contact rings 388 with the seal rings 382 sandwiched in between, and securing the contact rings 388 to one another with the seal rings 382 sandwiched in between. Thus, the insulating rings 404, the holding rings 390 and the contact rings 388 interlock in a structural engagement which resists axial movement of one ring from an adjacent ring. The insulating rings 404 also lengthen the electrical arc path between adjacent contact rings 388, providing the same advantages described above. The insulating rings 404 are preferably made from an implantable-grade. electrically non-conductive, rigid plastic material, such as PolyEtherEtherKetone (PEEK). However, in other embodiments the insulating rings 404 could be formed from materials having, different properties. If the insulating rings 404 are rigid, they may advantageously control compressive and tensile displacement of the components during assembly and during lead insertion.

In one embodiment of a method of assembling the connector assembly 380 of FIG. 13, the spring contacts 30 are placed within the grooves 50 in the contact rings 388, and the seal rings 382 are positioned within respective ones of the insulating rings 404. The first holding ring 390 is then interlocked with a first seal ring 382 and first insulating ring 404 in coaxial alignment with the insulating ring 404 overlapping the first holding ring 390 and the flanges 392 on the first holding ring 390 engaging the flanges on the first insulating ring 404. A first contact ring 388 is then interlocked with the first seal ring 382 and first insulating ring 404 in coaxial alignment with the insulating ring 404 overlapping the first contact ring 388 and the flange on the first insulating ring 404 seating within the groove 398 on the first contact ring 388 in interlocking engagement. Successive seal rings 382/insulating rings 404 and contact rings 388 are then added in interlocking coaxial alignment until a desired number of contact rings 388 have been added. Each time a new ring is added, it interlocks with the previously added ring with the insulating rings 404 snapping onto grooves 398 on the contact rings 388. A second holding ring 390 is then interlocked in coaxial alignment with the last added seal ring 382/insulating ring 404, opposite the first holding ring 390, with the flanges 384 on the second holding ring 390 and last added seal ring 382/insulating ring 404 engaging one another. To overlap the insulating rings 404 with the contact rings 388 and the holding rings 390, the chamfers 412 on each component are placed against one another and compression is then applied to force the insulating rings 404 to expand and ride up over the contact rings 388 until the flanges 410 snap into the grooves 398 in interlocking engagement. Thus, the interlocking of the components is a structural engagement which resists axial movement of one component from an adjacent component. In certain embodiments, the assembly process may be performed by hand without tools. The interlocking engagement of the components advantageously provides stability to the assembly as it is being assembled, retaining all components in coaxial alignment without the need for a dowel or assembly pin. However, in alternative assembly methods a dowel or assembly pin (not shown) may be used. The dowel or pin first receives a holding ring, and then the other components are slid onto the pin and into engagement with the earlier placed components.

Figure 14B:
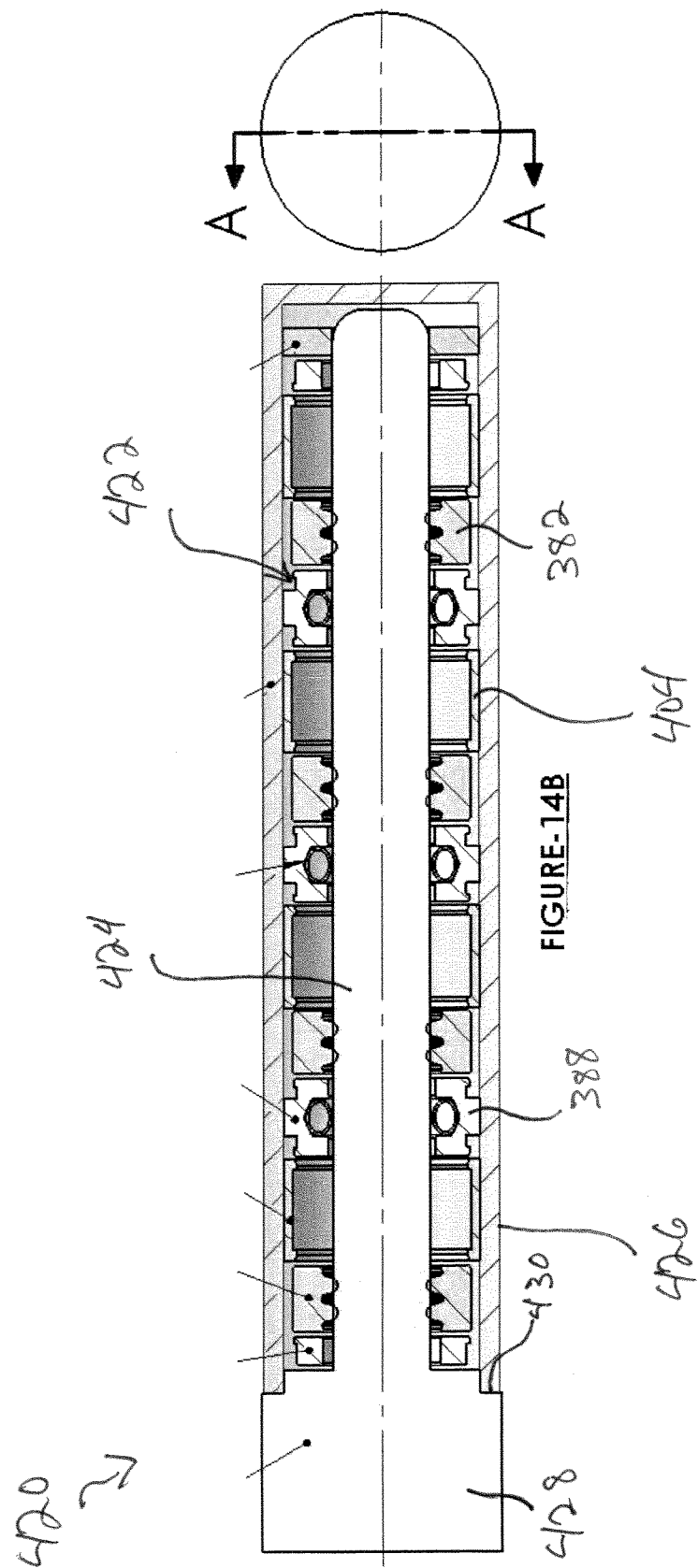
FIG. 14B is a front cross-sectional view of the kit of FIG. 14A in an assembled state.

FIGS. 14A and 14B illustrate another alternative embodiment 420 of the present connector assemblies. The embodiment 420 comprises pre-assembled connector components 422 configured to be transported from an assembly location to another location where the assembled components 422 are combined with a header (not shown) or other electronic devices or components. FIG. 14A illustrates the components 422 in an exploded state, and FIG. 14B illustrates the components 422 in an assembled state. Thus, FIGS. 14A and 14B may be viewed as a kit for storing, shipping, or transporting an assembled connector assembly.

The assembled components 422 are supported by a cylindrical pin 424, and contained within a cylindrical tube 426. In FIGS. 14A and 14B, the pin 424 includes an integral head 428 having a larger diameter than the main pin body, and a seat 430 configured mate with the open mouth 432 of the tube 426. The tube 426 is preferably made from a sturdy material, such as a rigid plastic or a metal. The tube 426 may be transparent for easy identification of the components 422 inside. The pin head 428 may be secured to the tube mouth 432 with adhesive, for example, for greater integrity. The tube 426 may also be hermetically sealed to prevent intrusion of contaminants.

Figure 14C:
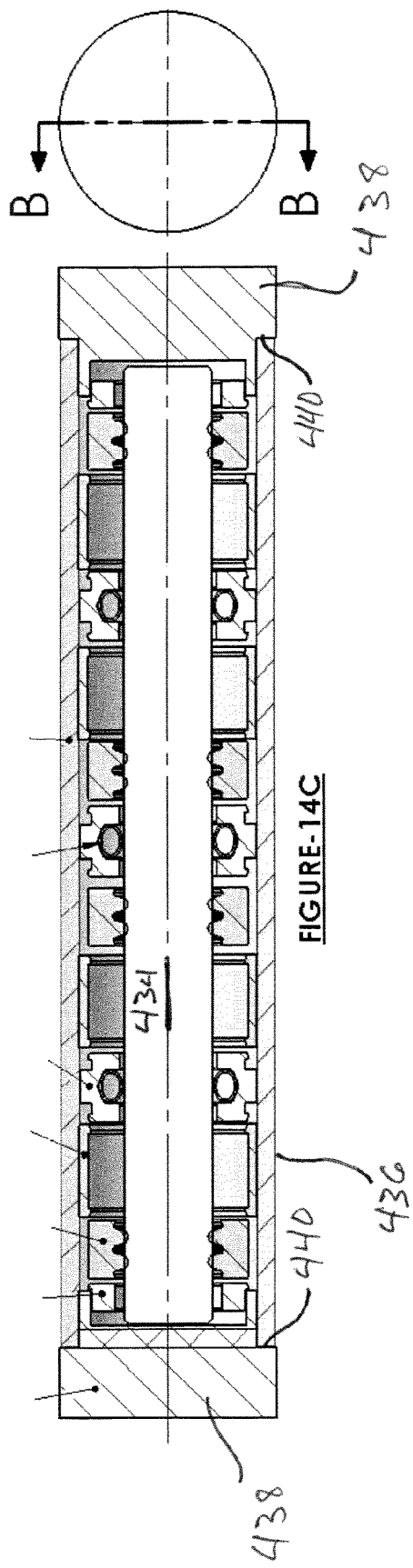
FIG. 14C is a front cross-sectional view of another embodiment of a kit including a connector assembly for use with IMDs or alternatively for transmitting multiple signals in an electrical-related application.

FIG. 14C illustrates an alternative embodiment in which the pin 434 does not have an integral head and the tube 436 is open at both ends. First and second end caps 438 include mating seats 440 to receive the open ends of the tube 436 and seal the tube 436.

In one embodiment, the assembled components 422 may be provided as a finished product for sale to customers who may then combine the assembled components 422 with any other device, such as an implantable medical device (IMD), for sale to end users. Thus, with reference to FIG. 14B one embodiment comprises a kit 420 including a container 426 containing a plurality of conductive contact rings 388, a plurality of non-conductive seal rings 382, and a pin 424 supporting the contact rings 388 and seal rings 382. The kit 420 may be assembled and packaged by a first party at a first location, then sold and shipped to a second party at a second location where the assembled components 422 are combined with an IMD, which IMD is then sold and shipped to a third party for implantation within a patient. The sturdy container 426, which may be sealed, maintains the integrity of the assembled components 422, protects the components 422 from handling damage, and resists intrusion of contaminants so that the components 422 remain clean. The present embodiments thus facilitate ease of integration of the assembled components 422 into the next process in the manufacturing flow of an IMD.

In the illustrated embodiment, the assembled components 422 are structurally similar to those of the embodiment of FIG. 13. Thus, the components 422 include conductive contact rings 388, non-conductive seal rings 382. and rigid plastic insulating rings 404. The components 422 may interlock in a structural engagement which resists axial movement of one component from an adjacent component as previously described. However, the structure of the components 422 is not limiting to the embodiment of FIG. 14. Rather, the scope of the embodiment of FIG. 14 is broad enough to encompass any set of assembled components 422 including alternating contact rings and seal rings.

In the present embodiments, all interfaces between seal rings and any other surface, including electrical leads, contact rings, holding rings, insulating rings, and spacers, may include an interference fit to enhance sealing. Further, in the foregoing examples of methods of assembling the present embodiments, the order of operations may be changed. Thus, the recited orders of steps are not limiting. Further, also in the foregoing examples of methods of assembling the present embodiments, steps such as cleaning and testing of the components may also be performed.

Several example embodiments of the present apparatus and methods for making the same have been described and illustrated. However, many modifications and variations will be apparent to those skilled in the art. For example, various materials may be changed, such as using two or more different materials or composites, different mechanical engagement means may be used to attach the various components to one another, making a sealing ring from multiple pieces rather than a singularly molded piece, etc. Moreover, the connector assembly may be used for any device that requires an in-line connection in which multiple conductive sources are to be relayed between a source generator and a source receiver, whether that device is configured for implanting or otherwise. Also while certain connector stacks are shown and disclosed for use with a three node or three electrode terminal lead cable or other integers thereof, the number of seal elements, ring contact elements, and canted-coil springs are not limited to the embodiments shown and can include more or less depending on the particular application. Accordingly, it is to be understood that the connector assemblies constructed according to principles herein may be embodied in other than as specifically described herein. Furthermore, while specific features may be discussed for one embodiment but not others, the same specific features may be understood to be usable with the other embodiments provided the specific features are compatible and not internally conflict.

The above description presents the best mode contemplated for carrying out the present connector assemblies for use with implantable medical devices, and of the manner and process of making and using it, in such full, clear, concise, and exact terms as to enable any person skilled in the art to which it pertains to make and use these connector assemblies. These connector assemblies is, however, susceptible to modifications and alternate constructions from that discussed above that are fully equivalent. Consequently, these connector assemblies are not limited to the particular embodiments disclosed. On the contrary, these connector assemblies cover all modifications and alternate constructions coming within the spirit and scope of the connector assemblies as generally expressed by the following claims, which particularly point out and distinctly claim the subject matter of the connector assemblies.

What is claimed is:

1. A connector assembly, comprising:
   a plurality of electrically conductive ring contact elements arranged coaxially, each ring contact element including an annular groove about its inner circumference;
   a plurality of electrically conductive garter-type spring contact elements positioned within the grooves; and
   a plurality of electrically non-conductive seal rings interposed between adjacent ones of the ring contact elements and arranged coaxially therewith;
   wherein the ring contact elements and the seal rings engage one another in an interlocking snap fit fashion to resist axial separation of the ring contact elements and the seal rings from one another in the absence of applied compression.

2. The connector assembly of claim 1, wherein each seal ring comprises pockets that receive thickened portions of the ring contact elements to achieve the interlocking.

3. The connector assembly of claim 1, wherein the contact rings and seal rings include interlocking annular flanges and grooves.

4. The connector assembly of claim 1, wherein the assembly is configured to receive a medical lead cable including a lead body for carrying a plurality of electrode leads, each lead including electrode terminals for providing electrical stimulation to body tissues at a stimulation site.

5. The connector assembly of claim 1, further comprising first and second holding rings positioned at opposite ends of the assembly and arranged coaxially with the ring contact elements.

6. The connector assembly of claim 1, wherein each seal ring includes a portion that protrudes outwardly beyond outer surfaces of the contact rings.

7. A connector assembly, comprising:
   a plurality of electrically conductive ring contact elements arranged coaxially, each ring contact element including an inner annular groove about an inner circumference and an outer annular groove about an outer surface;
   a plurality of electrically conductive spring contact elements positioned within the inner annular grooves; and
   a plurality of electrically non-conductive seal rings interposed between adjacent ones of the ring contact elements and arranged coaxially therewith;
   wherein each of the seal rings protrudes radially beyond outer surfaces of the ring contact elements; and
   wherein the outer annular groove of each ring contact element aligns with an inwardly extending annular flange on an inner surface of each ring contact element.

8. The connector assembly of claim 7, wherein protruding portions of the seal rings are configured to bear against inner surfaces of a pre-molded header in sealing engagement therewith.

9. The connector assembly of claim 7, wherein the contact rings and seal rings include interlocking annular flanges and grooves.

10. The connector assembly of claim 7, wherein the outer annular groove of each ring contact element is located closer to one end of the ring contact element than another end.

11. The connector assembly of claim 10, wherein the inner annular groove of each ring contact element is defined by two inwardly extending annular flanges.

12. The connector assembly of claim 7, wherein each of the seal rings includes an inwardly extending annular flange having undercuts on either side.

13. The connector assembly of claim 7, wherein the assembly is configured to receive a medical lead cable including a lead body for carrying a plurality of electrode leads, each lead including electrode terminals for providing electrical stimulation to body tissues at a stimulation site.

14. The connector assembly of claim 7, further comprising first and second holding rings positioned at opposite ends of the assembly and arranged coaxially with the ring contact elements.

15. A method of assembling a connector assembly, the method comprising:
   positioning a plurality of electrically conductive garter-type spring contact elements within grooves of a plurality of electrically conductive ring contact elements;
   interlocking a first seal ring with a first one of the ring contact elements such that the first seal ring and the first ring contact element are coaxial, the first seal ring being electrically non-conductive; and
   interlocking successive seal rings and ring contact elements in coaxial alignment with a snap fit engagement, and with the seal rings interposed between adjacent ones of the ring contact elements, until a desired number of ring contact elements have been added;
   wherein the interlocked seal rings and ring contact elements resist separation of the ring contact elements and the seal rings from one another in the absence of applied compression.

16. The method of claim 15, further comprising interlocking a first holding ring in coaxial alignment with the first seal ring and opposite the first ring contact element.

17. The method of claim 16, further comprising interlocking a second holding ring with a last added one of the ring contact elements and in coaxial alignment therewith.

18. The method of claim 15, further comprising interlocking a first insulating ring with the first contact ring and the first insulating ring surrounding the first seal ring.

19. The method of claim 18, wherein the first insulating ring is constructed of a rigid plastic.

20. The method of claim 15, further comprising performing the method by hand without tools.

* * * * *

UNITED STATES PATENT AND TRADEMARK OFFICE
CERTIFICATE OF CORRECTION

PATENT NO. : 8,167,660 B2
APPLICATION NO. : 12/876775
DATED : May 1, 2012
INVENTOR(S) : Farshid Dilmaghanian et al.

It is certified that error appears in the above-identified patent and that said Letters Patent is hereby corrected as shown below:

In column 1, line 16, delete "automotive" and insert -- automotive. --, therefor.

In column 4, line 9, delete "application:" and insert -- application; --, therefor.

In column 4, line 15, delete "11:" and insert -- 11; --, therefor.

In column 6, line 32, delete "1." and insert -- 1, --, therefor.

In column 6, line 34, delete "46. 48" and insert -- 46, 48 --, therefor.

In column 6, line 36, delete "46. 48" and insert -- 46, 48 --, therefor.

In column 6, line 38, delete "46. 48" and insert -- 46, 48 --, therefor.

In column 6, line 41, delete "shape." and insert -- shape, --, therefor.

In column 6, line 44, delete "be." and insert -- be, --, therefor.

In column 6, line 44, delete "example." and insert -- example, --, therefor.

In column 6, line 45, delete "Ranch." and insert -- Ranch, --, therefor.

In column 6, line 55, delete "However." and insert -- However, --, therefor.

In column 6, line 57, delete "46. 48" and insert -- 46, 48 --, therefor.

In column 8, line 6, delete "rings" and insert -- rings 32 --, therefor.

In column 8, line 8, delete "rings" and insert -- rings 32 --, therefor.

In column 9, line 24, delete "housing" and insert -- housing in --, therefor.

In column 12, line 8, delete "5." and insert -- 5, --, therefor.

In column 12, line 42, delete "assembly." and insert -- assembly, --, therefor.

In column 18, line 25, delete "tit" and insert -- fit --, therefor.

In column 20, line 42, delete "12A." and insert -- 12A, --, therefor.

In column 20, lines 45-67, delete "Each contact ring 342 includes a mating groove 350 at the ......................................discussed above." and insert the same on Col. 20, Line 44 as a continuation of the Paragraph.

Signed and Sealed this
Fourth Day of December, 2012

David J. Kappos
*Director of the United States Patent and Trademark Office*

CERTIFICATE OF CORRECTION (continued)
U.S. Pat. No. 8,167,660 B2

In column 20, line 48, delete "12A." and insert -- 12A, --, therefor.

In column 20, line 56, delete "Thus." and insert -- Thus, --, therefor.

In column 21, line 50, delete "assembled." and insert -- assembled, --, therefor.

In column 21, line 54, delete ",pin" and insert -- pin --, therefor.

In column 22, line 54, delete "grade." and insert -- grade, --, therefor.

In column 22, line 57, delete "having," and insert -- having --, therefor.

In column 23, line 19, delete "390." and insert -- 390, --, therefor.

In column 24, line 20, delete "382." and insert -- 382, --, therefor.

In column 25, line 1, delete "lull," and insert -- full, --, therefor.